United States Patent
Matsubara et al.

(10) Patent No.: US 9,456,977 B2
(45) Date of Patent: Oct. 4, 2016

(54) CATIONIZED GLYCEROLATED CELLULOSE

(71) Applicant: KAO CORPORATION, Tokyo (JP)

(72) Inventors: Masaki Matsubara, Wakayama (JP); Eisuke Miyoshi, Wakayama (JP); Yumi Yamaguchi, Wakayama (JP); Tomoko Uchiyama, Wakayama (JP); Naoyuki Yamazaki, Wakayama (JP); Ryosuke Fujii, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/384,915

(22) PCT Filed: Mar. 12, 2013

(86) PCT No.: PCT/JP2013/057581
§ 371 (c)(1),
(2) Date: Sep. 12, 2014

(87) PCT Pub. No.: WO2013/137474
PCT Pub. Date: Sep. 19, 2013

(65) Prior Publication Data
US 2015/0064128 A1    Mar. 5, 2015

(30) Foreign Application Priority Data

Mar. 13, 2012 (JP) ................... 2012-056452
Mar. 13, 2012 (JP) ................... 2012-056453
Jul. 24, 2012 (JP) ................... 2012-163416
Jul. 24, 2012 (JP) ................... 2012-163420

(51) Int. Cl.
| A61K 8/73 | (2006.01) |
| C08B 11/145 | (2006.01) |
| A61Q 19/10 | (2006.01) |
| A61Q 5/02 | (2006.01) |
| A61Q 5/12 | (2006.01) |
| C08B 11/20 | (2006.01) |
| C08L 1/28 | (2006.01) |
| A61K 8/58 | (2006.01) |
| A61Q 5/00 | (2006.01) |

(52) U.S. Cl.
CPC ............... *A61K 8/731* (2013.01); *A61K 8/585* (2013.01); *A61Q 5/00* (2013.01); *A61Q 5/02* (2013.01); *A61Q 5/12* (2013.01); *A61Q 19/10* (2013.01); *C08B 11/20* (2013.01); *C08L 1/284* (2013.01); *C08L 1/288* (2013.01)

(58) Field of Classification Search
None
See application file for complete search history.

(56) References Cited

FOREIGN PATENT DOCUMENTS

| DE | 3301667 A1 | 7/1984 |
| JP | 2004-262838 A | 9/2004 |
| JP | 2006-347972 A | 12/2006 |

OTHER PUBLICATIONS

International Search Report, issued in PCT/JP2013/057581, dated Jun. 26, 2013.

*Primary Examiner* — H. Sarah Park
(74) *Attorney, Agent, or Firm* — Birch, Stewart, Kolasch & Birch, LLP

(57) ABSTRACT

A cationized glycerolated cellulose which, when blended in a hair cosmetic, is able to impart excellent smoothness and its long-lasting feeling at the time of rinsing and to impart a moist feeling and softness to the hair after drying and, when blended in a skin cleanser, is able to impart an excellent moisturizing feeling after drying; a surfactant composition containing the same; and a hair cosmetic composition and a skin cleanser composition each containing the surfactant composition, are provided. [1] A cationized glycerolated cellulose having a specified structure, which has a main chain derived from an anhydroglucose, wherein a degree of substitution of a cationized alkylene oxy group per the anhydroglucose unit is from 0.01 to 0.18, and a degree of substitution of a glycerol group per the anhydroglucose unit is from 0.5. to 5.0; [2] a surfactant composition containing the above-described cationized glycerolated cellulose, a surfactant, and water; [3] a use of the above-described surfactant composition as a hair cosmetic composition and a skin cleanser composition; and [4] a hair cosmetic composition and a skin cleanser composition each containing the above-described cationized glycerolated cellulose, a surfactant, and water, are disclosed.

20 Claims, No Drawings

CATIONIZED GLYCEROLATED CELLULOSE

FIELD OF THE INVENTION

The present invention relates to a cationized glycerolated cellulose and also to a surfactant composition, a hair cosmetic composition, and a skin cleanser composition each containing the same.

BACKGROUND OF THE INVENTION

Hairs are damaged by the living environment (e.g., ultraviolet rays or heat by sunlight, and drying), the daily hair care behavior (e.g., shampooing, brushing, and heat by a dryer), or the chemical treatment (e.g., coloring, perming, etc.), and when the hairs rub against each other in a wet state, a large frictional force is generated on the surfaces, so that a feeling of friction or entanglement is presented during shampooing. In hair cosmetics, in addition to a basic function to remove the hair stains, in order to enhance finger combability, smoothness, and a long-lasting feeling of smoothness at the time of rinsing, a cationic polymer represented by a cationized hydroxyethyl cellulose is generally blended as a conditioning polymer.

For example, Patent Document 1 discloses a cleanser composition composed of a cationized hydroxyethyl cellulose having a quaternary nitrogen-containing group introduced thereinto, a surfactant, a water-soluble ester derived from a plant oil, and a pseudo cationic polyamine and describes that in hair care products such as a shampoo, etc., an effect for making the hair after cleansing smooth and soft is exhibited.

In addition, Patent Document 2 discloses a hair cosmetic composition containing a cationized glycerolated cellulose in which an average addition mole number of a cationic group is from 0.2 to 0.5, and an average addition mole number of a glycerol group is from 1 to 2.58 and describes that combability through the hair at the time of cleansing is excellent.

However, the techniques of Patent Documents 1 and 2 were not on a thoroughly satisfactory level in smoothness and its long-lasting feeling at the time of rinsing.

In addition, for example, Patent Document 3 discloses that a skin cleanser composition containing from 5 to 40% by weight of an anionic surfactant, from 0.5 to 20% by weight of a cationic polymer, and from 0.1 to 20% by weight of an oil having a viscosity at 25° C. of from 1 to 10,000 mPa·s provides a moisturizing effect after cleansing and also imparts a good feeling of touch.

PRIOR ART DOCUMENTS

Patent Documents

[Patent Document 1] JP-A-2006-347972
[Patent Document 2] German Patent No. 3301667
[Patent Document 3] JP-A-2004-262838

SUMMARY OF THE INVENTION

The present invention relates to the following [1] to [4].

[1] A cationized glycerolated cellulose having a main chain derived from an anhydroglucose represented by the following general formula (1), wherein a degree of substitution of a cationized alkylene oxy group per the anhydroglucose unit is from 0.01 to 0.18, and a degree of substitution of a glycerol group per the anhydroglucose unit is from 0.5 to 5.0.

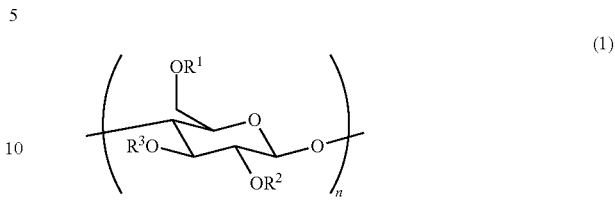

(In the formula, each of $R^1$, $R^2$, and $R^3$ independently indicates a substituent composed of one or more repeating units selected among the following formulae (2) to (5), or a hydrogen atom, provided that all of $R^1$, $R^2$, and $R^3$ in the molecule are not a hydrogen atom at the same time; and n indicates an average polymerization degree of the main chain derived from an anhydroglucose and is a number of from 100 to 12,000.)

(In the formulae, a repeating unit structure represented by the formula (2) or (3) indicates a cationized alkylene oxy group; a repeating unit structure represented by the formula (4) or (5) indicates a glycerol group; each of $R^4$ to $R^9$ independently indicates a linear or branched alkyl group having a carbon number of from 1 to 3; $X^-$ and $Y^-$ indicate an anion; r and s indicate any integer of from 0 to 3; and in the repeating unit structures represented by the formulae (2) to (5), the oxygen atom is bound to a hydrogen atom or a carbon atom of other repeating unit.)

[2] A surfactant composition containing the cationized glycerolated cellulose as set forth above in [1], a surfactant, and water.

[3] A use of the surfactant composition as set forth above in [2] as a hair cosmetic composition.

[4] A use of the surfactant composition as set forth above in [2] as a skin cleanser composition.

Effect of the Invention

According to the present invention, it is possible to provide a cationized glycerolated cellulose which, when blended in a hair cosmetic, is able to impart excellent smoothness and its long-lasting feeling at the time of rinsing and to impart a moist feeling and softness to the hair after drying and, when blended in a skin cleanser, is able to impart an excellent moisturizing feeling after drying; and a surfactant composition, a hair cosmetic composition, and a skin cleanser composition each containing the same.

DETAILED DESCRIPTION OF THE INVENTION

A problem of the present invention is to provide a cationized glycerolated cellulose which, when blended in a hair cosmetic, is able to impart excellent smoothness and its long-lasting feeling at the time of rinsing and to impart a moist feeling and softness to the hair after drying and, when blended in a skin cleanser, is able to impart an excellent moisturizing feeling after drying; and a surfactant composition, a hair cosmetic composition, and a skin cleanser composition each containing the same.

The present inventors have found that the foregoing problem can be solved by a specified cationized glycerolated cellulose and a surfactant composition containing the same.

[Cationized Glycerolated Cellulose]

The cationized glycerolated cellulose (hereinafter also referred to as "CGC") according to the present invention has a main chain derived from an anhydroglucose represented by the following general formula (1), wherein a degree of substitution of a cationized alkylene oxy group per the anhydroglucose unit is from 0.01 to 0.18, and a degree of substitution of a glycerol group per the anhydroglucose unit is from 0.5 to 5.0.

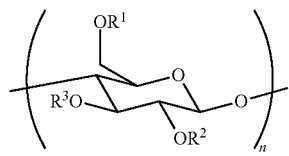
(1)

In the general formula (1), each of $R^1$, $R^2$, and $R^3$ independently indicates a substituent composed of one or more repeating units selected among the following formulae (2) to (5), or a hydrogen atom, provided that all of $R^1$, $R^2$, and $R^3$ in the molecule are not a hydrogen atom at the same time; and n indicates an average polymerization degree of the main chain derived from an anhydroglucose and is a number of from 100 to 12,000.

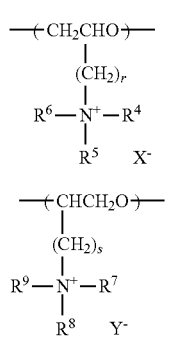
(2)

(3)

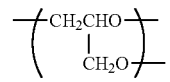
(4)

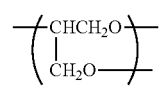
(5)

In the formulae (2) to (5), a repeating unit structure represented by the formula (2) or (3) indicates a cationized alkylene oxy group; a repeating unit structure represented by the formula (4) or (5) indicates a glycerol group; each of $R^4$ to $R^9$ independently indicates a linear or branched alkyl group having a carbon number of from 1 to 3; $X^-$ and $Y^-$ indicate an anion; r and s indicate any integer of from 0 to 3; and in the repeating unit structures represented by the formulae (2) to (5), the oxygen atom is bound to a hydrogen atom or a carbon atom of other repeating unit.

(Substituents $R^1$, $R^2$, and $R^3$)

In the foregoing general formula (1), in the case where the substituent $R^1$ is a substituent composed of one or more repeating units selected among the formulae (2) to (5), the substituent $R^1$ may be a substituent composed of plural repeating units selected among the formulae (2) to (5) or may be a substituent in which a hydrogen atom is bound to the oxygen atom of only one repeating unit selected among the formulae (2) to (5).

In addition, in the case where the substituent $R^1$ is a substituent composed of plural repeating units selected among the formulae (2) to (5), between the repeating units, the oxygen atom of one of the repeating units is bound to the carbon atom of the other repeating unit, and the oxygen atom not bound to the carbon atom of other repeating unit, for example, the oxygen atom positioned at an end of the substituent, is bound to a hydrogen atom.

In addition, a combination of the repeating units is not particularly limited. Plural repeating units of one member selected among the formulae (2) to (5) may be bound to each other, or repeating units of from 2 to 4 members selected from the formulae (2) to (5) may be bound to each other. In the general formula (1), in the case where $R^1$ is a substituent having a cationized alkylene oxy group and a glycerol group, a binding form between the cationized alkylene oxy group and the glycerol group may be like a block co-polymer, a random co-polymer, or an alternate co-polymer, and the binding form like a block co-polymer is preferable from the viewpoint of easiness of manufacture.

Specific examples of the substituent composed of plural repeating units selected among the formulae (2) to (5) include structures represented by the following formulae (6) to (8).

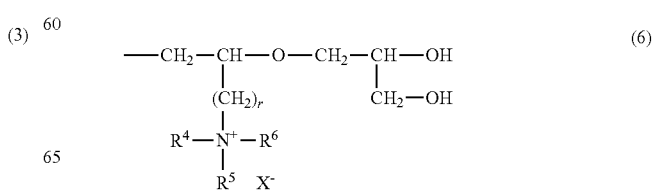
(6)

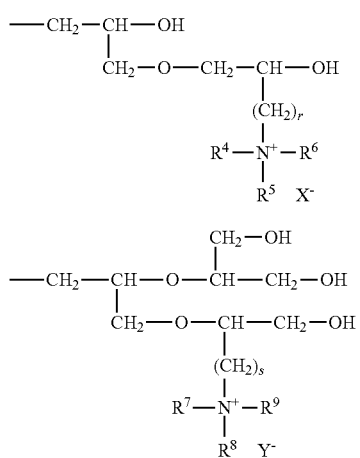

In the case where the substituent $R^1$ is a substituent composed of one or more repeating units selected among the formulae (2) to (5), the carbon atom at an end thereof is bound to the oxygen atom of the hydroxyl group of the main chain derived from an anhydroglucose.

Incidentally, in the case where the substituent $R^1$ is a substituent composed of one or more repeating units selected among the formulae (2) to (5), the subject substituent may contain a repeating unit of other structure than the repeating units of the formulae (2) to (5) so far as the effects of the present invention are not impaired.

In the case where the substituent $R^2$ is a substituent composed of one or more repeating units selected among the formulae (2) to (5), a mode of the subject substituent is the same as the mode in the case where the substituent $R^1$ is a substituent composed of one or more repeating units selected among the formulae (2) to (5).

In the case where the substituent $R^3$ is a substituent composed of one or more repeating units selected among the formulae (2) to (5), a mode of the subject substituent is the same as the mode in the case where the substituent $R^1$ is a substituent composed of one or more repeating units selected among the formulae (2) to (5).

The substituents $R^1$, $R^2$, and $R^3$ are independent upon each other and may be the same as or different from each other, provided that all of the substituents $R^1$, $R^2$, and $R^3$ in the molecule are not a hydrogen atom at the same time.

(Cationized Alkylene Oxy Group Represented by the Formula (2) or (3))

In the foregoing formula (2) or (3), each of $R^4$ to $R^9$ is independently a linear or branched alkyl group having a carbon number of from 1 to 3, and specific examples thereof include a methyl group, an ethyl group, an n-propyl group, and an isopropyl group. Of, these, from the viewpoint of water solubility of CGC, a methyl group and an ethyl group are preferable, and a methyl group is more preferable.

In the formulae (2) and (3), $X^-$ and $Y^-$ indicate an anion, which is a counter ion of the quaternary ammonium ion. $X^-$ and $Y^-$ are not particularly limited so far as they are an anion, and specific examples thereof include an alkyl sulfate ion (having a carbon number of 1 or more and not more than 3), a sulfuric acid ion, a phosphoric acid ion, a fatty acid ion (having a carbon number of 1 or more and not more than 3), a halide ion, and the like.

Of these, from the viewpoint of easiness of manufacture, one or more members selected among an alkyl sulfate ion (having a carbon number of 1 or more and not more than 3), a sulfuric acid ion, and a halide ion are preferable, and a halide ion is more preferable. Examples of the halide ion include a fluoride ion, a chloride ion, a bromide ion, and an iodide ion. From the viewpoints of water solubility and chemical stability of CGC, a chloride ion and a bromide ion are preferable, and a chloride ion is more preferable.

r and s indicate any integer of from 0 to 3. From the viewpoint of easiness of availability of the raw material, r and s are preferably 1.

(Degree of Substitution of Cationized Alkylene Oxy Group)

In the present invention, a degree of substitution of the cationized alkylene oxy group (also referred to as "MS (N+)") refers to an average value of the number of cationized alkylene oxy groups existing in the molecule of CGC per one anhydroglucose unit constituting the main chain. The MS (N+) is measured and calculated by the method described in the working examples as described later.

The MS (N+) in the cationized glycerolated cellulose according to the present invention is from 0.01 to 0.18. So far as the MS (N+) falls within this range, after treating an object, in particular, the hair with the surfactant composition containing CGC according to the present invention, it is possible to obtain favorable smoothness and its long-lasting feeling at the time of rinsing and a sufficient moist feeling and softness after drying and also to obtain a moisturizing feeling after cleansing the skin. From this viewpoint, the MS (N+) is preferably 0.03 or more, more preferably 0.06 or more, still more preferably 0.08 or more, and yet still more preferably 0.1 or more, and preferably not more than 0.17, more preferably not more than 0.16, and still more preferably not more than 0.15.

In addition, from the viewpoint of obtaining favorable smoothness, long-lasting feeling, and moisturizing feeling as described above, the MS (N+) is preferably from 0.03 to 0.17, more preferably from 0.06 to 0.16, still more preferably from 0.08 to 0.15, and yet still more preferably from 0.1 to 0.15.

(Degree of Direct Substitution of Cationized Alkylene Oxy Group: DS(N+))

In CGC according to the present invention, an average value of the number of cationized alkylene oxy groups substituted directly on the hydroxyl groups of the main chain derived from an anhydroglucose per one anhydroglucose is referred to as a degree of direct substitution of the cationized alkylene oxy group (DS(N+)).

From the viewpoint of, after treating an object, in particular, the hair with the surfactant composition containing CGC according to the present invention, obtaining favorable smoothness and its long-lasting feeling at the time of rinsing and a moist feeling and softness after drying and also the viewpoint of obtaining a moisturizing feeling after cleansing the skin, a value of DS(N+) is preferably 0.001 or more, and more preferably 0.020 or more. The value of DS(N+) does not exceed the above-described upper limit of MS (N+) in view of the definition thereof. Incidentally, in the present invention, the DS(N+) is specifically calculated by the method described in the working examples.

(Degree of Substitution of Glycerol Group)

In the present invention, a degree of substitution of the glycerol group (also referred to as "MS(Gly)") refers to an average value of the number of glycerol groups existing in the CGC molecule per one anhydroglucose unit constituting the main chain. The MS(Gly) is measured and calculated by the method described in the working examples as described later.

The MS(Gly) in the cationized glycerolated cellulose according to the present invention is from 0.5 to 5.0. So far as the MS(Gly) falls within this range, after treating an object, in particular, the hair with the surfactant composition containing CGC according to the present invention, it is possible to obtain favorable smoothness and its long-lasting feeling at the time of rinsing and a sufficient moist feeling and softness after drying and also to obtain a moisturizing feeling after cleansing the skin. In addition, so far as the MS(Gly) falls within this range, since the solubility of CGC in the surfactant composition is high, blending is easy. From these viewpoints, the MS(Gly) is preferably 0.6 or more, more preferably 0.8 or more, and still more preferably 1.0 or more. From the above-described viewpoints and the viewpoint of costs of CGC according to the present invention, the MS(Gly) is preferably not more than 4.0, more preferably not more than 3.0, still more preferably not more than 2.5, and yet still more preferably not more than 2.0.

In addition, from the viewpoint of obtaining favorable smoothness and long-lasting feeling and moist feeling, softness and moisturizing feeling after drying as described above and also the viewpoint of solubility of CGC in the surfactant composition, the MS(Gly) is preferably from 0.6 to 4.0, more preferably from 0.8 to 3.0, still more preferably from 0.8 to 2.5, and yet still more preferably from 1.0 to 2.0.

(Degree of Direct Substitution of Glycerol Group: DS(Gly))

In CGC according to the present invention, an average value of the number of glycerol groups substituted directly on the hydroxyl groups of the main chain derived from an anhydroglucose per one anhydroglucose is referred to as a degree of direct substitution of the glycerol group (DS (Gly)).

From the viewpoint of solubility of CGC in the surfactant composition, in particular, after treating the hair with the surfactant composition containing CGC according to the present invention, from the viewpoint of obtaining favorable smoothness and its long-lasting feeling at the time of rinsing and a moist feeling and softness after drying and also from the viewpoint of obtaining a moisturizing feeling after cleansing the skin, DS(Gly) is preferably 0.1 or more, more preferably 0.6 or more, and still more preferably 0.7 or more. A value of DS(Gly) does not exceed the above-described upper limit of MS(Gly) in view of the definition thereof. Incidentally, in the present invention, the DS(Gly) is specifically calculated by the method described in the working examples.

(Other Substituents)

In CGC according to the present invention, as other substituent than the cationized alkylene oxy group and the glycerol group, which may be substituted, there is exemplified a hydrophobic group. The hydrophobic group as referred to herein means a hydrocarbon group having a carbon number of 7 or more. Examples of the hydrocarbon group include an alkyl group, an alkenyl group, an aryl group, an aralkyl group, an alkaryl group, and the like.

In CGC according to the present invention, from the viewpoint of easiness of manufacture, a degree of substitution of the hydrophobic group is preferably less than 0.01, more preferably not more than 0.005, still more preferably not more than 0.001, and yet still more preferably 0.

The degree of substitution of the hydrophobic group refers to an average value of the number of hydrophobic groups existing in the molecule of CGC per one anhydroglucose unit constituting the main chain.

The degree of substitution of the hydrophobic group can be calculated from a content % (% by mass) of the hydrophobic group contained in CGC obtained by a method in conformity with the Zeisel method which is known as a technique for analyzing an average addition mole number of an alkoxy group of cellulose ether, as described in *Analytical Chemistry*, Vol. 51, No. 13, 2172 (1979), *The Japanese Pharmacopoeia Fifteenth Edition* (Section of Analysis Method of Hydroxypropylcellulose), and the like.

From the viewpoint of easiness of manufacture, it is preferable that CGC according to the present invention does not substantially contain other substituent than the cationized alkylene oxy group and the glycerol group.

(Cation Charge Density)

From the viewpoint of, after treating an object, in particular, the hair with the surfactant composition containing CGC according to the present invention, obtaining favorable smoothness and its long-lasting feeling at the time of rinsing and a moist feeling and softness after drying and also the viewpoint of obtaining a moisturizing feeling after cleansing the skin, a cation charge density of CGC according to the present invention is preferably 0.05 mmol/g or more, more preferably 0.1 mmol/g or more, still more preferably 0.2 mmol/g or more, yet still more preferably 0.25 mmol/g or more, and especially preferably 0.3 mmol/g or more, and preferably not more than 0.8 mmol/g, more preferably not more than 0.7 mmol/g, still more preferably not more than 0.6 mmol/g, and especially preferably not more than 0.5 mmol/g.

In addition, from the viewpoint of obtaining favorable smoothness and its long-lasting feeling, and moist feeling, softness, and moisturizing feeling after drying as described above, the cation charge density is preferably from 0.05 to 0.8 mmol/g, more preferably from 0.1 to 0.7 mmol/g, still more preferably from 0.2 to 0.6 mmol/g, yet still more preferably from 0.25 to 0.6 mmol/g, and especially preferably from 0.3 to 0.5 mmol/g.

In the present invention, the cation charge density refers to a mole number of cation charges contained per gram of CGC and is calculated according to the following calculation equation.

$$\text{Cation charge density}(\text{mmol/g}) = MS(N+)/(74.1 \times MS(Gly) + a \times MS(N+) + 162.1) \times 1000$$

(In the equation, 74.1 and 162.1 are a molecular weight of the glycerol group and a molecular weight of the anhydroglucose unit, respectively; and "a" indicates a molecular weight of the cationized alkylene oxy group.)

(Average Polymerization Degree of CGC)

In CGC according to the present invention, an average polymerization degree n of the main chain derived from an anhydroglucose refers to a viscosity average polymerization degree measured by the cuprous ammoniacal process described in the working examples. Though the average polymerization degree n varies depending upon an average polymerization degree of cellulose serving as a raw material of CGC or a manufacturing method of CGC, so far as it is 100 or more and not more than 12,000, in particular, favorable smoothness and its long-lasting feeling are obtained at the time of rinsing after treating the hair with CGC according to the present invention.

From the viewpoint of in particular, after treating the hair, obtaining favorable smoothness and its long-lasting feeling at the time of rinsing and a moist feeling and softness after drying and also the viewpoint of obtaining a moisturizing feeling after cleansing the skin, the average polymerization degree n is preferably 200 or more, more preferably 500 or more, and still more preferably 1,000 or more. In addition, from the viewpoint of handling properties of CGC and the surfactant composition having CGC blended therein according to the present invention, the average polymerization degree n is preferably not more than 10,000, more preferably not more than 5,000, and still more preferably not more than 2,500.

In addition, from the viewpoint of obtaining favorable smoothness and its long-lasting feeling, and moist feeling, softness, and moisturizing feeling after drying as described above and also the viewpoint of handling properties as described above, the average polymerization degree n is preferably from 200 to 10,000, more preferably from 500 to 5,000, and still more preferably from 1,000 to 2,500.

(Aqueous Solution Viscosity of Cationized Glycerolated Cellulose)

In the present invention, an aqueous solution viscosity refers to a viscosity of a 1% by mass aqueous solution measured at 25° C. using a B type viscometer, and specifically, it is measured by the method described in the working examples.

In general, it is known that an average polymerization degree n of a cellulose derivative correlates with an aqueous solution viscosity of the cellulose derivative, and that the higher the average polymerization degree n, the higher the aqueous solution viscosity is. The aqueous solution viscosity varies depending upon not only the average polymerization degree, but the charge density of a solute, the presence of an insoluble matter or a semi-soluble matter, crosslinking, and the like. From the viewpoint of in particular, after treating the hair, obtaining favorable smoothness and its long-lasting feeling at the time of rinsing and also the viewpoint of obtaining a moisturizing feeling after cleansing the skin, the aqueous solution viscosity of CGC is preferably 1 mPa·s or more, more preferably 10 mPa·s or more, and still more preferably 20 mPa·s or more. In addition, from the viewpoint of handling properties of the blended surfactant composition, the aqueous solution viscosity of CGC is preferably not more than 100,000 mPa·s, more preferably not more than 10,000 mPa·s, and still more preferably not more than 6,000 mPa·s.

In addition, from the viewpoint of obtaining favorable smoothness and its long-lasting feeling and moisturizing feeling as described above and also the viewpoint of handling properties as described above, the aqueous solution viscosity of CGC is preferably from 1 to 100,000 mPa·s, more preferably from 10 to 10,000 mPa·s, and still more preferably from 20 to 6,000 mPa·s.

[Manufacture of CGC]

CGC according to the present invention can be manufactured by allowing cellulose to react with a cationizing agent corresponding to the cationized alkylene oxy group of CGC according to the present invention (hereinafter also referred to simply as "cationizing agent") and a glycerolating agent. Here, the order of the glycerolation reaction and the cationization reaction is not particularly limited, and either of them may be first carried out, or the both may be carried out at the same time or may be alternately repeated.

The cellulose, the cationizing agent, and the glycerolating agent used for raw materials of the manufacture of CGC according to the present invention are hereunder described in detail.

<Raw Material Cellulose>

The type of the cellulose which is used for a raw material of CGC according to the present invention (hereinafter also referred to as "raw material cellulose") is not particularly limited. From the viewpoints of a cellulose purity, a polymerization degree, and easiness of availability, various wood chips; and pulps such as wood pulps manufactured from woods, cotton linter pulps obtained fibers in the surroundings of cotton seeds, etc. are preferable.

From the viewpoint of in particular, after treating the hair, obtaining favorable smoothness and its long-lasting feeling at the time of rinsing and a moist feeling and softness after drying and also the viewpoint of obtaining a moisturizing feeling after cleansing the skin, an average polymerization degree of the raw material cellulose is preferably 100 or more, more preferably 200 or more, still more preferably 500 or more, and yet still more preferably 1,000 or more. From the same viewpoints, the average polymerization degree of the raw material cellulose is preferably not more than 12,000, more preferably not more than 10,000, still more preferably not more than 5,000, and yet still more preferably not more than 2,500. In addition, from the viewpoint of obtaining favorable smoothness and its long-lasting feeling, and moist feeling, softness, and moisturizing feeling after drying as described above, the average polymerization degree of the raw material cellulose is preferably from 100 to 12,000, more preferably from 200 to 10,000, still more preferably from 500 to 5,000, and yet still more preferably from 1,000 to 2,500.

Incidentally, the average polymerization degree of the raw material cellulose refers to a viscosity average polymerization degree measured by the cuprous ammoniacal process described in the working examples, or the like.

The shape of the raw material cellulose is not particularly limited so far as the introduction into a manufacturing apparatus is not hindered. However, from the viewpoint of operation, the shape of the raw material cellulose is preferably a sheet form, a pellet form, a chip form, or a powdered form, more preferably a chip form or a powdered form, and still more preferably a powdered form.

<Glycerolating Agent>

Examples of the glycerolating agent which is used for the manufacture of CGC according to the present invention include glycidol; 3-halo-1,2-propanediols such as 3-chloro-1,2-propanediol, 3-bromo-1,2-propanediol, etc.; glycerin; glycerin carbonate; and the like. Of these, glycidol is preferable from the viewpoints of the fact that a salt is not formed as a by-product and high reactivity.

These glycerolating agents can be used either alone or in combination of two or more kinds thereof.

The amount of the glycerolating agent to be used may be properly chosen taking into consideration the desired MS(Gly). From the viewpoints of water solubility of CGC and in particular, after treating the hair, obtaining favorable smoothness and its long-lasting feeling at the time of rinsing and a moist feeling and softness after drying and also the viewpoint of obtaining a moisturizing feeling after cleansing the skin, the amount of the glycerolating agent to be used is preferably 0.2 moles or more, more preferably 0.4 moles or more, and still more preferably 1 mole or more, and preferably not more than 60 moles, more preferably not more than 20 moles, and still more preferably not more than 10 moles, per mole of the anhydroglucose unit (hereinafter also referred to as "AGU") of the raw material cellulose. In addition, from the viewpoint of obtaining favorable smoothness and its long-lasting feeling, and moist feeling, softness, and moisturizing feeling after drying as described above, the amount of the glycerolating agent to be used is preferably from 0.2 to 60 moles, more preferably from 0.4 to 20 moles, and still more preferably from 1 to 10 moles per mole of AGU.

An addition method of the glycerolating agent may be any of batchwise addition, intermittent addition, or continuous addition. However, from the viewpoint of increasing a reaction yield of the glycerolating agent with the raw material cellulose, continuous addition is preferable.

<Cationizing Agent>

Examples of the cationizing agent which is used for the manufacture of CGC according to the present invention include compounds represented by the following general formulae (9) and (10), and the like.

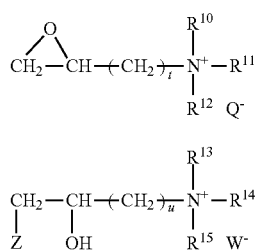

In the general formulae (9) and (10), $R^{10}$ to $R^{15}$ and preferred modes thereof are the same as those in $R^4$ to $R^9$ in the foregoing general formulae (2) and (3). t and u and preferred modes thereof are the same as those in r in the foregoing formula (2). $Q^-$ and $W^-$ and preferred modes thereof are the same as those in $X^-$ in the foregoing formula (2). Z indicates a halogen atom. $R^{10}$ to $R^{15}$ may be the same as or different from each other.

Specific examples of the compounds represented by the foregoing general formulae (9) and (10) include a chloride, a bromide, or an iodide of each of glycidyltrimethylammonium, glycidyltriethylammonium, and glycidyltripropylammonium; 3-chloro-2-hydroxypropyltrimethylammonium, 3-chloro-2-hydroxypropyltriethylammonium, and 3-chloro-2-hydroxypropyltripropylammonium, each of which is a chloride; 3-bromo-2-hydroxypropyltrimethylammonium, 3-bromo-2-hydroxypropyltriethylammonium, and 3-bromo-2-hydroxypropyltripropylammonium, each of which is a bromide; and 3-iodo-2-hydroxypropyltrimethylammonium, 3-iodo-2-hydroxypropyltriethylammonium, and 3-iodo-2-hydroxypropyltripropylammonium, each of which is an iodide.

Of these, from the viewpoints of easiness of availability of the raw material and chemical stability, a chloride or a bromide of glycidyltrimethylammonium or glycidyltriethylammonium; 3-chloro-2-hydroxypropyltrimethylammonium or 3-chloro-2-hydroxypropyltriethylammonium as a chloride; and 3-bromo-2-hydroxypropyltrimethylammonium or 3-bromo-2-hydroxypropyltriethylammonium as a bromide are preferable. Of these, glycidyltrimethylammonium chloride and 3-chloro-2-hydroxypropyltrimethylammonium chloride are more preferable.

These cationizing agents can be used either alone or in combination of two or more kinds thereof.

The amount of the cationizing agent to be used may be properly chosen taking into consideration the desired MS (N+) and the reaction yield. From the viewpoints of water solubility of CGC and, in particular, after treating the hair, obtaining favorable smoothness and its long-lasting feeling at the time of rinsing and a moist feeling and softness after drying and also the viewpoint of obtaining a moisturizing feeling after cleansing the skin, the amount of the cationizing agent to be used is preferably 0.01 moles or more, more preferably 0.03 moles or more, and still more preferably 0.05 moles or more, and preferably not more than 10 moles, more preferably not more than 8 moles, and still more preferably not more than 5 moles, per mole of AGU of the raw material cellulose. In addition, from the viewpoint of obtaining favorable smoothness and its long-lasting feeling, and moist feeling, softness, and moisturizing feeling after drying as described above, the amount of the cationizing agent to be used is preferably from 0.01 to 10 moles, more preferably from 0.03 to 8 moles, and still more preferably from 0.05 to 5 moles, per mole of AGU of the raw material cellulose.

An addition method of the cationizing agent may be any of batchwise addition, intermittent addition, or continuous addition. However, from the viewpoint of increasing a reaction yield of cationization into the raw material cellulose, continuous addition is preferable.

<Manufacturing Method of Cationized Glycerolated Cellulose (CGC)>

CGC according to the present invention can be manufactured by allowing the raw material cellulose to react with the cationizing agent and the glycerolating agent. Though a manufacturing method thereof is not particularly limited, in general, cellulose has high crystallinity, so that its reactivity is poor. Accordingly, it is preferable to carry out a treatment of lowering the crystallinity to improve the reactivity. Examples of such a manufacturing method of CGC include the following methods (i) to (iii).

Method (i): An activation method generally called mercerization, namely a method in which the raw material cellulose, a large amount of water, and a large excess of an alkali metal hydroxide are mixed to obtain an alkali cellulose, which is then allowed to react with the cationizing agent and the glycerolating agent.

Method (ii): A method in which the raw material cellulose is uniformly dissolved using a solvent capable of dissolving cellulose therein, as described in Encyclopedia of Cellulose, edited by The Cellulose Society of Japan and published by Asakura Publishing Co., Ltd., *Macromol. Chem. Phys.*, 201, 627-631 (2000), and the like, for example, dimethyl sulfoxide containing tetrabutylammonium fluoride, dimethyl sulfoxide containing p-formaldehyde, dimethylacetamide containing lithium chloride, etc., and the raw material cellulose is then allowed to react with the cationizing agent and the glycerolating agent.

Method (iii): A method in which the raw material cellulose in a powdered form, a pellet form, or a chip form is allowed to react with the cationizing agent and the glycerolating agent in the copresence of an alkali without using an excess of water or a solvent, different from the methods (i) and (ii).

Among the foregoing methods (i) to (iii), the method (iii) is preferable from the viewpoints of operability and productivity, the viewpoint of, after treating the hair, obtaining smoothness and its long-lasting feeling at the time of rinsing, and also the viewpoint of obtaining a moisturizing feeling after cleansing the skin. The method (iii) is hereunder more specifically described.

The method (iii) is a method in which after undergoing the following steps (1) and (2) to achieve reaction and activation of cellulose, glycerolation reaction and cationization reaction are carried out to manufacture CGC.

Step (1): A step of pulverizing the raw material cellulose in the presence of an alkali compound in an amount of 0.6 molar equivalents or more and not more than 1.5 molar equivalents to one mole of AGU of the raw material cellulose and also in the presence of water in an amount of not more than 10% by mass relative to the raw material cellulose, thereby obtaining a cellulose powder mixture.

Step (2): A step of adding water to the cellulose powder mixture obtained in the step (1) to adjust a water content in the cellulose powder mixture at 30% by mass or more and not more than 100% by mass relative to the raw material cellulose used in the step (1), thereby obtaining a powdered alkali cellulose.

(Step (1))

The water content at the time of pulverization in the step (1) is preferably low. Though a lower limit of the water content at the time of pulverization is 0% by mass relative to the raw material cellulose, it is difficult to control the water content to 0% by mass. Accordingly, the water content is preferably 0.01% by mass or more, more preferably 0.1% by mass or more, and still more preferably 1% by mass or more relative to the raw material cellulose. In addition, the water content at the time of pulverization is preferably not more than 10% by mass, more preferably not more than 7% by mass, and still more preferably not more than 6% by mass relative to the raw material cellulose. In addition, the water content at the time of pulverization in the step (1) is preferably from 0.01 to 10% by mass, more preferably from 0.1 to 7% by mass, and still more preferably from 1 to 6% by mass relative to the raw material cellulose.

Examples of the alkali compound which is used in the step (1) include alkali metal hydroxides such as sodium hydroxide, potassium hydroxide, lithium hydroxide, etc., alkaline earth metal hydroxides such as magnesium hydroxide, calcium hydroxide, etc., tertiary amines such as trimethylamine, triethylamine, etc., and the like. Of these, alkali metal hydroxides and alkaline earth metal hydroxides are preferable, alkali metal hydroxides are more preferable, and sodium hydroxide and potassium hydroxide are still more preferable. These alkali compounds can be used either alone or in combination of two or more kinds thereof.

From the viewpoints of an enhancement of reaction activity of cellulose and reaction selectivity on the basis of the glycerolating agent or cationizing agent at the time of glycerolation reaction or cationization reaction as described later, the amount of the alkali compound at the time of pulverization is preferably 0.6 molar equivalents or more, more preferably 0.7 molar equivalents or more, and still more preferably 0.8 molar equivalents or more per mole of AGU of the raw material cellulose. In addition, from the viewpoints of an enhancement of reaction activity of cellulose and reaction selectivity on the basis of the glycerolating agent or cationizing agent at the time of glycerolation reaction or cationization reaction as described later, the amount of the alkali compound at the time of pulverization is preferably not more than 1.5 molar equivalents, more preferably not more than 1.3 molar equivalents, and still more preferably not more than 1.2 molar equivalents per mole of AGU of the raw material cellulose.

From the viewpoints of the above-described enhancement of reaction activity of cellulose and the above-described reaction selectivity, the amount of the alkali compound at the time of pulverization is preferably from 0.6 to 1.5 molar equivalents, more preferably from 0.7 to 1.3 molar equivalents, and still more preferably from 0.8 to 1.2 molar equivalents per mole of AGU of the raw material cellulose.

An addition method of the alkali compound is not particularly limited, and it may be either batchwise addition or divided addition.

Though a form of the alkali compound at the time of addition is not particularly limited, from the viewpoint of pulverization efficiency, the alkali compound is preferably a solid. In the case of adding the alkali compound in a state of solid, from the viewpoint of handling properties at the time of manufacture and also the viewpoint of uniformly dispersing the alkali compound into the raw material cellulose, the alkali compound is preferably in a pellet form, a granular form, or a powdered form, and more preferably in a pellet form or a granular form. Incidentally, the matter that the alkali compound is a solid does not mean that it does not contain moisture. The alkali compound may contain moisture due to moisture absorption of moisture in air, or the like.

A pulverizer which is used in the step (1) is not particularly limited, and it may be an apparatus capable of powdering the raw material cellulose and dispersing the alkali compound into the raw material cellulose as far as possible.

Specific examples of the pulverizer include roll mills such as a high-pressure compression roll mill, a roll rotating mill, etc., vertical roller mills such as a ring roller mill, a roller race mill, a ball race mill, etc., container driving-type mills such as a rolling ball mill, a vibration ball mill, a vibration rod mill, a vibration tube mill, a planetary ball mill, a centrifugal fluidization mill, etc., media-stirring mills such as a tower pulverizer, an agitation tank mill, a flowing tank mill, an annular mill, etc., compaction shearing mills such as a high-speed centrifugal roller mill, an ang mill, etc., a mortar, a stone hand mill, a mass colloider, a fret mill, an edge-runner mill, a knife mill, a pin mill, a cutter mill, and the like.

Of these, from the viewpoints of pulverization efficiency of cellulose and productivity, container driving-type mills and media-stirring mills are preferable; container driving-type mills are more preferable; vibration mills such as a vibration ball mill, a vibration rod mill, a vibration tube mill, etc. are still more preferable; a vibration rod mill is yet still more preferable. A pulverization method may be either a batchwise mode or a continuous mode.

A material of the apparatus and/or the grinding medium which is used for the pulverization is not particularly limited, and examples thereof include iron, stainless steel, alumina, zirconia, silicon carbide, silicon nitride, glass, and the like. From the viewpoint of pulverization efficiency of the raw material cellulose, iron, stainless steel, zirconia, silicon carbide, and silicon nitride are preferable, and furthermore, from the viewpoint of industrial utilization, iron and stainless steel are especially preferable.

From the viewpoint of pulverization efficiency of the raw material cellulose, in the case where the apparatus used is a vibration mill, and the grinding medium is a rod, from the viewpoint of pulverization efficiency, an outer diameter of the rod is preferably 0.1 mm or more, and more preferably 0.5 mm or more, and preferably not more than 100 mm, and more preferably not more than 50 mm. In addition, from the viewpoint of pulverization efficiency, the outer diameter of the rod is preferably from 0.1 to 100 mm, and more preferably from 0.5 to 50 mm.

Though a filling percentage of the rod in terms of its suitable range varies depending upon the type of the vibration mill, it is preferably 10% or more, and more preferably 15% or more, and preferably not more than 97%, and more preferably not more than 95%. In addition, the filling percentage of the rod is preferably from 10 to 97%, and more preferably from 15 to 95%. So far as the filling percentage falls within this range, it is possible to enhance a frequency of contact between cellulose and the rod and also to enhance the pulverization efficiency without inhibiting the movement of the grinding medium. Here, the filling percentage refers to an apparent volume of the rod relative to a capacity of a stirring portion of the vibration mill.

Though the temperature at the time of pulverization is not particularly limited, from the viewpoint of suppression of decomposition of cellulose and also the viewpoint of operation costs, it is preferably −100° C. or higher, more preferably 0° C. or higher, and still more preferably 30° C. or higher, and preferably not higher than 200° C., more preferably not higher than 100° C., and still more preferably not higher than 70° C. In addition, from the viewpoint of suppression of decomposition of cellulose and also the viewpoint of operation costs as described above, the temperature at the time of pulverization is preferably from −100° C. to 200° C., more preferably from 0 to 100° C., and still more preferably from 30 to 70° C.

The time of pulverization may be properly adjusted such that the raw material cellulose is powdered. Though the time of pulverization varies depending upon the pulverizer used, the amount of energy used, and the like, it is generally 1 minute or more and not more than 12 hours. From the viewpoint of sufficiently carrying out the pulverization, the time of pulverization is preferably 3 minutes or more, more preferably 4 minutes or more, and still more preferably 5 minutes or more, and from the viewpoint of productivity, the time of pulverization is preferably not more than 3 hours, more preferably not more than 1 hour, and still more preferably not more than 20 minutes. In addition, from the viewpoint of sufficiently carrying out the pulverization and also the viewpoint of productivity, the time of pulverization is preferably from 3 minutes to 3 hours, more preferably from 4 minutes to 1 hour, and still more preferably from 5 minutes to 20 minutes.

(Step (2))

The step (2) is a step of adding water to the cellulose powder mixture obtained in the step (1) to adjust the water content in the cellulose powder mixture at 30% by mass or more and not more than 100% by mass relative to the raw material cellulose used in the step (1), thereby obtaining a powdered alkali cellulose. From the viewpoint of uniformly dispersing water into the cellulose powder mixture, it is preferable to add water to the cellulose powder mixture, followed by stirring and mixing, or to add and mix water while stirring the cellulose powder mixture.

An addition method of water is not particularly limited, and it may be either batchwise addition or divided addition. In the case of adding batchwise water, it is preferable to spray water.

From the viewpoint of avoiding coloration of the produced alkali cellulose, the addition of the alkali compound, the addition of water, and aging are preferably carried out in an inert gas atmosphere such as nitrogen, etc. as the need arises.

(Glycerolation Reaction and Cationization Reaction)

CGC can be obtained by allowing the alkali cellulose manufactured by the foregoing steps (1) and (2) (hereinafter also referred to simply as "alkali cellulose") to react with the glycerolating agent and the cationizing agent to carryout the glycerolation reaction and the cationization reaction.

An addition method at the time of adding the glycerolating agent and the cationizing agent to the alkali cellulose is not particularly limited, and it may be any of batchwise addition, divided addition, or continuous addition, or combined addition thereof. From the viewpoint of efficiently dispersing the glycerolating agent and the cationizing agent into the alkali cellulose, it is preferable to continuously or dividedly add the glycerolating agent and the cationizing agent while stirring the alkali cellulose.

Forms of the glycerolating agent and the cationizing agent at the time of addition are not particularly limited. In the case where the glycerolating agent and the cationizing agent are in a liquid state, they may be used as they are, or they may be used in a diluted form with a good solvent of the glycerolating agent and the cationizing agent, such as water, a non-aqueous solvent, etc.

Examples of the non-aqueous solvent which is used for the dilution include generally used secondary or tertiary lower alcohols having a carbon number of 3 or 4, such as isopropanol, tert-butanol, etc.; ketones having a carbon number of 3 or more and not more than 6, such as acetone, methyl ethyl ketone, methyl isobutyl ketone, etc.; ether solvents such as tetrahydrofuran, 1,4-dioxane, ethylene glycol dimethyl ether, diethylene glycol dimethyl ether, etc.; aprotic polar solvents such as dimethyl sulfoxide, etc.; and the like.

From the viewpoint of the reaction yield of the glycerolating agent and the cationizing agent, the glycerolation reaction and the cationization reaction can also be carried out in the presence of a non-aqueous solvent. As the non-aqueous solvent, the same non-aqueous solvent as that described above can be used.

From the viewpoint of addition effect of such a non-aqueous solvent, the use amount of the non-aqueous solvent is preferably 0% by mass or more, more preferably 30% by mass or more, and still more preferably 50% by mass or more, and from the viewpoints of productivity and reaction yield of the glycerolating agent and the cationizing agent, preferably not more than 1,000% by mass, more preferably not more than 300% by mass, and still more preferably not more than 200% by mass, relative to the raw material cellulose of the step (1). In addition, from the viewpoint of addition effect of the non-aqueous solvent and also the viewpoint of productivity and the above-described reaction yield, the use amount of the non-aqueous solvent is preferably from 0 to 1,000% by mass, more preferably from 30 to 300% by mass, and still more preferably from 50 to 200% by mass relative to the raw material cellulose of the step (1).

Examples of apparatus which can be used for the glycerolation reaction and the cationization reaction include mixers capable of achieving agitation, such as a Loedige mixer, etc., and mixing machines such as so-called kneaders, which are used for kneading a powder, a high-viscosity substance, a resin, or the like, etc.

From the viewpoint of reaction rate, the temperature at the time of glycerolation reaction and cationization reaction is preferably 0° C. or higher, more preferably 20° C. or higher, and still more preferably 30° C. or higher, and from the viewpoint of suppression of decomposition of the glycerolating agent, the cationizing agent, or the alkali cellulose, the temperature at the time of glycerolation reaction and cationization reaction is preferably not higher than 200° C., more preferably not higher than 100° C., and still more preferably not higher than 80° C. In addition, from the viewpoints of reaction rate and suppression of decomposition of the glycerolating agent, the cationizing agent, or the alkali cellulose, the temperature at the time of glycerolation reaction and cationization reaction is preferably from 0 to 200° C., more preferably from 20 to 100° C., and still more preferably from 30 to 80° C.

The reaction time may be properly adjusted by the reaction rate of the glycerolating agent and the cationizing agent, the introduction amount of a desired ether group, and the like. The reaction time is generally 0.1 hours or more and not more than 72 hours. From viewpoint of reaction yield of the glycerolating agent and the cationizing agent, the reaction time is preferably 0.2 hours or more, more preferably 0.5 hours or more, and still more preferably 1 hour or more, and from the viewpoint of productivity, the reaction time is preferably not more than 36 hours, more preferably not more than 18 hours, and still more preferably not more than 12 hours. In addition, from the viewpoint of suppression of decomposition of the glycerolating agent, the cationizing agent, or the alkali cellulose and also the viewpoint of productivity, the reaction time is generally from 0.1 to 72 hours, preferably from 0.2 to 36 hours, more preferably from 0.5 to 18 hours, and still more preferably from 1 to 12 hours.

Incidentally, from the viewpoint of suppressing coloration and a lowering of the molecular weight of a main chain derived from an anhydroglucose, the glycerolation reaction and the cationization reaction are preferably carried out in an inert gas atmosphere such as nitrogen, etc. as the need arises.

The order of the glycerolation reaction and the cationization reaction is not particularly limited.

After completion of the reaction, the alkali can be neutralized with an acid. As the acid, inorganic acids such as sulfuric acid, hydrochloric acid, phosphoric acid, etc., and organic acids such as acetic acid, lactic acid, etc. can be used.

If desired, the obtained CGC can also be used after separation by means of filtration or the like, or washing with hot water, a hydrated isopropyl alcohol or hydrated acetone solvent, or the like to remove the unreacted cationizing agent or glycerolating agent, a by-product derived from the cationizing agent or the glycerolating agent, or a salt formed as a by-product by means of neutralization or the like. Besides, general purification methods such as reprecipitation purification, centrifugation, dialysis, etc. can be adopted as a purification method.

[Surfactant Composition]

The surfactant composition according to the present invention contains CGC according to the present invention, a surfactant, and water.

<CGC>

From the viewpoint of in particular, after treating the hair, obtaining excellent smoothness and its long-lasting feeling at the time of rinsing and also the viewpoint of obtaining a moisturizing feeling after cleansing the skin, the content of CGC in the surfactant composition according to the present invention is preferably 0.01% by mass or more, more preferably 0.05% by mass or more, and still more preferably 0.10% by mass or more. In addition, from the viewpoint of handling properties of the surfactant composition, the content of CGC in the surfactant composition is preferably not more than 10% by mass, more preferably not more than 5% by mass, and still more preferably not more than 1% by mass. In addition, from the viewpoint of obtaining excellent smoothness and its long-lasting feeling and moisturizing feeling, the content of CGC in the surfactant composition is preferably from 0.01 to 10% by mass, more preferably from 0.05 to 5% by mass, and still more preferably from 0.10 to 1% by mass.

<Surfactant>

The surfactant composition according to the present invention contains one or more kinds of surfactants.

As the surfactant, any surfactant can be used so far as it is generally used for drugs, quasi-drugs, cosmetics, toiletries, miscellaneous goods, and the like. Specifically, examples thereof include one or two or more members selected among anionic surfactants, nonionic surfactants, cationic surfactants, and ampholytic surfactants.

In the case where the surfactant composition according to the present invention is used for hair cosmetics, from the viewpoint of, after treating the hair, obtaining favorable smoothness and its long-lasting feeling at the time of rinsing and a moist feeling and softness after drying, an anionic surfactant, a nonionic surfactant, an ampholytic surfactant, and a cationic surfactant are preferable. In addition, in the case where the hair cosmetic is a shampoo, from the viewpoints of cleansing properties, foamability, and foam quality, an anionic surfactant, a nonionic surfactant, and an ampholytic surfactant are preferable. In the case where the hair cosmetic is a hair treatment, a hair rinse, a hair conditioner, a hair cream, or the like, a nonionic surfactant and a cationic surfactant are preferable.

In the case where the surfactant composition according to the present invention is used for skin cleansing, from the viewpoint of imparting a moisturizing feeling after cleansing the skin and drying, an anionic surfactant, a nonionic surfactant, and an ampholytic surfactant are preferable.

(Anionic Surfactant)

Sulfuric acid ester salts, sulfonic acid salts, carboxylic acid salts, phosphoric acid ester salts, and amino acid salts, each having a hydrophobic site, are preferable as the anionic surfactant.

Specifically, examples thereof include sulfuric acid ester salts having a hydrophobic site, such as alkyl sulfates, alkenyl sulfates, polyoxyalkylene alkyl ether sulfates, polyoxyalkylene alkenyl ether sulfates, polyoxyalkylene alkylphenyl ether sulfates, etc.; sulfonic acid salts having a hydrophobic site, such as alkyl sulfosuccinates, polyoxyalkylene alkyl sulfosuccinates, alkane sulfonates, acyl isethionates, acyl methyl taurates, etc.; carboxylic acid salts having a hydrophobic site, such as higher fatty acid salts having a carbon number of 8 or more and not more than 16, polyoxyalkylene alkyl ether acetic acid salts, etc.; phosphoric acid ester salts having a hydrophobic site, such as alkyl phosphates, polyoxyalkylene alkyl ether phosphoric acid salts, etc.; amino acid salts having a hydrophobic site, such as acyl glutamates, alanine derivatives, glycine derivatives, arginine derivatives, etc.; and the like.

From the viewpoints of cleansing properties, foamability, and foam quality of the surfactant composition, and from the viewpoint of in particular, after treating the hair, obtaining excellent smoothness and its long-lasting feeling at the time of rinsing and also the viewpoint of obtaining a moisturizing feeling after cleansing the skin, the anionic surfactant has preferably an alkyl group or an alkenyl group having a carbon number of 8 or more, and more preferably an alkyl group or an alkenyl group having a carbon number of 10 or more, and the anionic surfactant has preferably an alkyl group or an alkenyl group having a carbon number of not more than 20, and more preferably an alkyl group or an alkenyl group having a carbon number of not more than 16, as a hydrophobic site. From the viewpoints of cleansing properties, foamability, and foam quality and also the viewpoint of obtaining smoothness and its long-lasting feeling and moisturizing feeling as described above, the above-described surfactant preferably has an alkyl group or an alkenyl group having a carbon number of from 8 to 20, and more preferably an alkyl group or an alkenyl group having a carbon number of from 10 to 16, as a hydrophobic site.

Of these, alkyl sulfates such as sodium lauryl sulfate, etc., polyoxyethylene alkyl ether sulfates such as sodium polyoxyethylene lauryl ether sulfate (sodium laureth-2 sulfate), etc., higher fatty acid salts such as potassium laurate, etc., polyoxyethylene alkyl ether acetates such as sodium polyoxyethylene lauryl ether acetate (sodium laureth-4,5 acetate), etc., alkyl sulfosuccinates such as sodium laureth-2 sulfosuccinate, etc., acyl glutamates such as sodium N-acyl-L-glutamate (sodium cocoyl glutamate), etc., acyl isethionates, and acyl methyl taurates are preferable; and polyoxyethylene alkyl ether sulfates and alkyl sulfates are more preferable.

(Nonionic Surfactant)

Examples of the nonionic surfactant include polyethylene glycol types such as polyoxyethylene sorbitan fatty acid esters, polyoxyethylene sorbite fatty acid esters, polyoxyethylene glycerin fatty acid esters, polyoxyethylene fatty acid esters, polyoxyethylene alkyl ethers, polyoxyethylene alkylphenyl ethers, polyoxyalkylene (hydrogenated) castor oils, etc., polyhydric alcohol types such as sucrose fatty acid esters, polyglycerin alkyl ethers, polyglycerin fatty acid esters, alkyl glucosides, etc., fatty acid alkanolamides, and the like.

From the viewpoints of cleansing properties of hair cosmetics and foam amount and foam quality at the time of cleansing and also the above-described viewpoints, the nonionic surfactant preferably has an alkyl group or an alkenyl group having a carbon number of 8 or more and not more than 20 as a hydrophobic site.

Of these, polyoxyalkylene alkyl ethers, polyoxyethylene hydrogenated castor oils, fatty acid alkanolamides, and alkyl glucosides are preferable; and alkyl glucosides having a carbon number of 8 or more and not more than 18, and preferably not more than 12, such as decyl glucoside, etc., polyoxyethylene alkyl ethers such as polyoxyethylene lauryl ether, polyoxyethylene cetyl/stearyl ether, etc., and fatty acid monoalkanolamides such as coconut fatty acid monoethanolamides, coconut fatty acid N-methylmonoethanolamides, etc. are more preferable. The carbon number of the alkyl glucoside is preferably from 8 to 18, and more preferably from 8 to 12.

(Ampholytic Surfactant)

Examples of the ampholytic surfactant include betaine based surfactants such as imidazoline based betaines, alkyldimethylamino acetic acid betaines, fatty acid amidopropyl betaines, sulfobetaines, etc., amine oxide type surfactants such as alkyldimethylamine oxides, etc., and the like.

Of these, from the viewpoints of cleansing properties of the surfactant composition and foam amount and foam quality at the time of cleansing and also the above-described viewpoints, imidazoline based betaines, alkyldimethylamino acetic acid betaines, fatty acid amidopropyl betaines, alkylhydroxy sulfobetaines, and the like are preferable. Specifically, coconut fatty acid amidopropyl betaines, lauryl carbomethoxymethylhydroxy imidazolium betaine, lauryl hydroxy sulfobetaine, and the like are preferable.

(Cationic Surfactant)

Examples of the cationic surfactant include mineral acid or organic acid salts of a tertiary amine represented by the following general formula (11) and quaternary ammonium salt type surfactants represented by the following general formula (12).

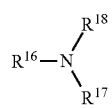
(11)

(In the formula, $R^{16}$ indicates a linear or branched alkyl group or alkenyl group having a carbon number of 6 or more and not more than 28, which may be divided by an amide group, an ester group, or an ether group; $R^{17}$ indicates a linear or branched alkyl group, alkenyl group, or alkanol group having a carbon number of 1 or more and not more than 28, which may be divided by an amide group, an ester group, or an ether group; and $R^{18}$ indicates a linear or branched alkyl group or alkanol group having a carbon number of 1 or more and not more than 3.)

In the general formula (11), from the viewpoint of, when used as a hair cosmetic, imparting smoothness of the hair and its long-lasting feeling at the time of rinsing and a moist feeling and softness after drying, $R^{16}$ is preferably a linear or branched alkyl group or alkenyl group, more preferably a linear or branched alkyl group, and still more preferably a linear alkyl group. In addition, from the same viewpoint as that described above, the carbon number of $R^{16}$ is preferably 12 or more and not more than 28, more preferably 14 or more and not more than 25, and still more preferably 16 or more and not more than 25. From the same viewpoint as that described above, $R^{17}$ is preferably a linear or branched alkyl group, alkenyl group, or alkanol group, more preferably a linear or branched alkyl group or alkanol group, and still more preferably a linear alkyl group or alkanol group. In addition, from the same viewpoint as that described above, the carbon number of $R^{17}$ is preferably 1 or more and not more than 4, or 12 or more and not more than 28, more preferably 1 or more and not more than 3, or 14 or more and not more than 25, and still more preferably 1 or more and not more than 2, or 16 or more and not more than 25. From the same viewpoint as that described above, $R^{18}$ is preferably a methyl group, an ethyl group, or a hydroxylethyl group.

Though the mineral acid or organic acid which forms a salt together with the tertiary amine represented by the general formula (11) is not particularly limited, from the viewpoint of dispersion stability of the surfactant, a hydrogen halide, sulfuric acid, acetic acid, citric acid, lactic acid, glutamic acid, and an alkyl sulfuric acid having a carbon number of 1 or more and not more than 3 are preferable. From the viewpoint of chemical stability, hydrogen chloride is preferable as the hydrogen halide.

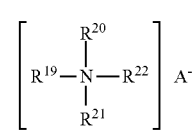
(12)

(In the formula, $R^{19}$ indicates a linear or branched alkyl group or alkenyl group having a carbon number of 6 or more and not more than 28, which may be divided by an amide group, an ester group, or an ether group; $R^{20}$ indicates a linear or branched alkyl group, alkenyl group, or alkanol group having a carbon number of 1 or more and not more than 28, which may be divided by an amide group, an ester group, or an ether group; $R^{21}$ and $R^{22}$ indicate a linear or branched alkyl group having a carbon number of 1 or more and not more than 3; and $A^-$ indicates an anion that is a counter ion of the ammonium salt.)

In the general formula (12), from the viewpoint of, when used as a hair cosmetic, imparting smoothness of the hair and its long-lasting feeling at the time of rinsing and a moist feeling and softness after drying, a preferred mode of $R^{19}$ is the same as the preferred mode of $R^{16}$ in the general formula (11). From the same viewpoint, a preferred mode of $R^{20}$ is the same as the preferred mode of $R^{17}$ in the general formula (11). In addition, from the same viewpoint, $R^{21}$ and $R^{22}$ are preferably a methyl group or an ethyl group.

$A^-$ is not particularly limited so far as it is an anion. Specific examples thereof include an alkyl sulfuric acid ion, a sulfuric acid ion, a phosphoric acid ion, an alkyl carboxylate, a halide ion, and the like. Of these, from the viewpoint of easiness of manufacture and availability, a halide ion is preferable. Examples of the halide ion include a fluoride ion, a chloride ion, a bromide ion, and an iodide ion. From the viewpoint of chemical stability, a chloride ion and a bromide ion are preferable, and a chloride ion is more preferable.

Examples of the mineral acid or organic acid salt of the tertiary amine represented by the general formula (11) and the quaternary ammonium salt type surfactant represented by the general formula (12) include mono-long-chain alkyltrimethylammonium chlorides, di-long-chain alkyldimethylammonium chlorides, and long-chain tertiary amine salts. Specifically, examples thereof include mono-long-chain alkyltrimethylammonium chlorides such as stearyltrimethylammonium chloride, behenyltrimethylammonium chloride, cetyltrimethylammonium chloride, stearoxypropyltrimethylammonium chloride, etc.; di-long-chain alkyldimethylammonium chlorides such as distearyldimethylammonium chloride, diisostearyldimethylammonium chloride; a mono-long-chain diethylamine, such as stearyldimethylamine, behenyldimethylamine, octadecyloxypropyldimethylamine, stearamidoethyldiethylamine, stearamidopropyldimethylamine, behenamidopropyldimethylamine; or glutamic acid, hydrochloric acid, citric acid, or lactic acid salts of a mono-long-chain dimethylamine; and the like. Of these, from the viewpoint of, when used as a hair cosmetic, imparting smoothness of the hair and its long-lasting feeling at the time of rinsing and a moist feeling and softness after drying, behenyltrimethylammonium chloride, cetyltrimethylammonium chloride, stearoxypropyltrimethylammonium chloride, stearamidopropyldimethylamine, and behenamidopropyldimethylamine are preferable.

(Content of Surfactant)

In the case where the surfactant composition according to the present invention is used as a hair cosmetic, from the viewpoint of, after treating the hair, obtaining excellent smoothness and its long-lasting feeling at the time of rinsing and a moist feeling and softness after drying, and in the case where the surfactant composition according to the present invention is used as a skin cleanser, from the viewpoint of obtaining an excellent moisturizing feeling after treating, rinsing, and drying the skin, the content of the surfactant in the surfactant composition according to the present invention is preferably 0.1% by mass or more, more preferably 0.5% by mass or more, still more preferably 1% by mass or more, and yet still more preferably 5% by mass or more, and preferably not more than 80% by mass, more preferably not more than 50% by mass, and still more preferably not more than 36% by mass. In addition, from the viewpoint of obtaining smoothness and its long-lasting feeling and moist feeling, softness, and moisturizing feeling after drying as described above, the content of the surfactant in the surfactant composition according to the present invention is preferably from 0.1 to 80% by mass, more preferably from 0.5 to 50% by mass, and still more preferably from 1 to 36% by mass.

In the case where the surfactant composition according to the present invention is used for hair cosmetics, from the above-described viewpoint, the content of the surfactant is yet still more preferably from 0.5 to 20% by mass, and especially preferably from 1 to 20% by mass.

In the case where the surfactant composition according to the present invention is used for skin cleansers, from the above-described viewpoint, the content of the surfactant is yet still more preferably from 5 to 36% by mass.

<Oil>

In the case where the surfactant composition according to the present invention is used as a hair cosmetic, from the viewpoint of obtaining a moist feeling and softness after treatment and drying, and in the case where the surfactant composition according to the present invention is used as a skin cleanser, from the viewpoint of obtaining an excellent moisturizing feeling after treating and drying the skin, the surfactant composition may further contain an oil.

As the oil, any oil can be used so far as it is an oily component which is generally used for drugs, quasi-drugs, cosmetics, toiletries, miscellaneous goods, and the like and is a sparingly water-soluble or water-insoluble oil having a dissolution amount of 0 g or more and not more than 1 g relative to 100 g of water at 20° C. From the above-described viewpoints, the dissolution amount of the oil is preferably 0 g or more and not more than 0.5 g, and more preferably 0 g or more and not more than 0.1 g relative to 100 g of water at 20° C.

From the above-described viewpoints, the oil is preferably one or two or more members selected among (i) an ester oil, (ii) a silicone oil, (iii) an ether oil, (iv) a hydrocarbon oil, (v) a higher alcohol, and (vi) a carboxylic acid having a hydrocarbon group having a carbon number of from 17 to 23 which may be substituted with a hydroxyl group.

From the same viewpoints as those described above, the ester oil (i) is preferably an ester oil represented by the following general formula (13), (14), or (16), a hydrophobic carboxylic acid ester of dipentaerythritol, or a dialkyl carbonate compound represented by general formula (17).

$$R^{23}\text{---COO---}R^{24} \tag{13}$$

(In the formula, $R^{23}$ indicates a linear or branched alkyl group having a carbon number of 8 or more and not more than 22; and $R^{24}$ indicates a linear or branched alkyl group or alkenyl group having a carbon number of 1 or more and not more than 22.)

From the same viewpoints as those described above, the carbon number of $R^{23}$ in the general formula (13) is preferably 10 or more and not more than 20, and more preferably 12 or more and not more than 18. From the same viewpoints as those described above, the carbon number of $R^{24}$ is preferably 1 or more and not more than 20, and more preferably 1 or more and not more than 18. $R^{24}$ is preferably a linear or branched alkyl group or alkenyl group having a carbon number of 1 or more and not more than 18, which may be divided by a propylene oxy group or a phenyl group.

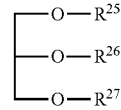

(14)

(In the formula, each of $R^{25}$, $R^{26}$, and $R^{27}$ independently indicates a hydrogen atom or a group represented by the general formula (15), provided that all of them are not a hydrogen atom at the same time.)

$$\text{---CO---}R^{28} \tag{15}$$

(In the formula, $R^{28}$ indicates a linear or branched alkyl group or alkenyl group having a carbon number of from 8 to 22, which may be divided by a carboxylic acid ester group and which may be substituted with a hydroxyl group.)

From the same viewpoints as those described above, the carbon number of $R^{28}$ in the general formula (15) is preferably 8 or more and not more than 20, and more preferably 8 or more and not more than 18.

Specific examples of the ester oil (i) represented by the general formula (13) or (14) include castor oil, cacao oil, mink oil, avocado oil, olive oil, sunflower oil, camellia oil, apricot-kernel oil, almond oil, wheat germ oil, theobroma grandiflorum seed oil, grape seed oil, babassu oil, jojoba oil, macadamia nut oil, camellia oleifera seed oil, shea butter oil, camellia reticulata seed oil, meadowfoam oil, beeswax, lanolin, hydrogenated lanolin, lanolin fatty acid octyl dodecyl, caprylyl eicosenoate, diisopropyl dimerate, myristyl 2-ethylhexanoate, cetyl 2-ethylhexanoate, stearyl 2-ethylhexanoate, octyl octanoate, lauryl octanoate, myristyl octanoate, isocetyl octanoate, octylpropylheptylate, cetostearyl isononanoate, isononyl isononanoate, isotridecyl isononanoate, methyl laurate, hexyl laurate, octyl laurate, isopropyl myristate, octyl myristate, myristyl myristate, octyldodecyl myristate, isopropyl palmitate, 2-ethylhexyl palmitate, octyl palmitate, cetyl palmitate, methyl oleate, oleyl oleate, decyl oleate, isobutyl oleate, methyl stearate, 2-ethylhexyl stearate, octyl stearate, isocetyl stearate, stearyl stearate, butyl stearate, isotridecyl stearate, isopropyl isostearate, isocetyl isostearate, isostearyl isostearate, propylene glycol isostearate, 2-ethylhexyl hydroxystearate, oleyl erucate, propanediol dicaprate, diisopropyl adipate, diethoxyethyl succinate, 2-ethylhexyl succinate, sucrose polysoyate, sucrose polybehenate, sucrose tetraisostearate, glyceryl tribehenate, hydroxyalkyl (C16-18) hydroxy dimer dilinoleyl ether, triisostearin, pentaerythrityl tetrastearate, and the like.

Of these ester oils, from the same viewpoints as those described above, sunflower oil, avocado oil, camellia oil, macadamia nut oil, shea butter oil, octyl laurate, octyl myristate, octyldodecyl myristate, isopropyl myristate, myristyl myristate, isopropyl palmitate, 2-ethylhexyl palmitate, octyl palmitate, cetyl palmitate, methyl stearate, 2-ethylhexyl stearate, octyl stearate, isocetyl stearate, stearyl stearate, butyl stearate, and isotridecyl stearate are preferable; and one or two or more members selected among sunflower oil, avocado oil, camellia oil, macadamia nut oil, shea butter oil, octyl laurate, octyl myristate, myristyl myristate, isopropyl palmitate, octyl palmitate, cetyl palmitate, octyl stearate, isocetyl stearate, stearyl stearate, isostearyl stearate, and isostearyl isostearate are more preferable.

$$R^{29}O\text{-}(AO)_m\text{—}COR^{30} \tag{16}$$

(In the formula, $R^{29}$ indicates a hydrocarbon group having a carbon number of 6 or more and not more than 20, which contains at least one substituted or unsubstituted aromatic ring; $R^{30}$ indicates a linear or branched alkyl group or alkenyl group having a carbon number of 1 or more and not more than 25; AO indicates an alkylene oxy group having a carbon number of 2 or more and not more than 4; m is a number of 1 or more and not more than 50; and when m is 2 or more, then AO groups of the number of m may be the same as or different from each other.)

From the same viewpoints as those described above, $R^{29}$ in the general formula (16) is preferably an aromatic hydrocarbon group having a carbon number of 6 or more and not more than 12, more preferably an aromatic hydrocarbon group having a carbon number of 6 or more and not more than 10, and still more preferably a benzyl group.

From the same viewpoints as those described above, $R^{30}$ is preferably an alkyl group having a carbon number of 7 or more and not more than 21, and more preferably an alkyl group having a carbon number of 11 or more and not more than 15.

From the same viewpoints as those described above, the AO group is preferably a propylene oxy group; and m is preferably 1 or more and not more than 10, and more preferably 1 or more and not more than 5.

Suitable examples of the ester oil represented by the general formula (16) include an ester of a 3-mole adduct of propylene oxide of benzyl alcohol with myristic acid (a trade name: CRODAMOL STS, available from Croda), an ester of a 3-mole adduct of propylene oxide of benzyl alcohol with 2-ethylhexanoic acid (a trade name: CRODAMOL SFX, available from Croda), and the like.

The hydrophobic carboxylic acid ester of dipentaerythritol refers to a compound obtained by dehydration condensation of dipentaerythritol and one or more hydrophobic carboxylic acids. Here, the hydrophobic carboxylic acid refers to a carboxylic acid having a hydrocarbon group having a carbon number of 16 or more and not more than 24 which may have a hydroxyl group. Specific examples of the hydrophobic carboxylic acid include palmitic acid, stearic acid, oleic acid, isostearic acid, hydroxystearic acid, rhodinic acid, and the like.

From the viewpoint of availability, an ester composed of a mixed acid of hydroxystearic acid, stearic acid, and rhodinic acid with dipentaerythritol is preferable.

$$R^{31}O(CH_2CH_2O)_vCO(OCH_2CH_2)_w\text{—}OR^{32} \tag{17}$$

(In the formula, each of $R^{31}$ and $R^{32}$ indicates a linear or branched alkyl group and/or alkenyl group having a carbon number of 6 or more and not more than 22; and each of v and w is 0 or a number of 1 or more and not more than 50.)

From the same viewpoints as those described above, $R^{31}$ and $R^{32}$ in the general formula (17) are preferably an alkyl group having a carbon number of 6 or more and not more than 18, and more preferably an alkyl group having a carbon number of 8 or more and not more than 12.

From the same viewpoints as those described above, v and w are preferably 0 or a number of 1 or more and not more than 5, and more preferably 0.

Suitable examples of the dialkyl carbonate compound represented by the general formula (17) include dioctyl carbonate (a trade name: CETIOL CC, available from Cognis) and the like.

From the same viewpoints as those described above, the silicone oil (ii) is preferably one or more members selected among dimethylpolysiloxane, dimethiconol (dimethylpolysiloxane having a hydroxyl group on an end thereof), amino-modified silicone (dimethylpolysiloxane having an amino group in a molecule thereof), polyether-modified silicone, glycerin-modified silicone, an amino derivative silicone, a silicone wax, and a silicone elastomer.

From the viewpoint of imparting a favorable moist feeling and softness to the hair after the treatment with the hair cosmetic according to the present invention and drying and also the viewpoint of dispersibility at the time of preparation of a hair cosmetic, a viscosity of the silicone oil (ii) is preferably 100,000 mm²/s or more and not more than 15,000,000 mm²/s.

From the same viewpoints as those described above, the ether oil (iii) is preferably a dialkyl ether compound represented by the following general formula (18).

$$R^{33}\text{—}O\text{—}R^{34} \tag{18}$$

(In the formula, each of $R^{33}$ and $R^{34}$ indicates a linear or branched alkyl group and/or alkenyl group having a carbon number of 6 or more and not more than 22.)

From the same viewpoints as those described above, $R^{33}$ and $R^{34}$ in the general formula (18) are preferably an alkyl group having a carbon number of 6 or more and not more than 18, and more preferably an alkyl group having a carbon number of 8 or more and not more than 12.

Suitable examples of the dialkyl ether compound represented by the general formula (18) include dioctyl ether (a trade name: CETIOL OE, available from Cognis) and the like.

From the same viewpoints as those described above, the hydrocarbon oil (iv) is preferably a saturated or unsaturated hydrocarbon having a carbon number of 20 or more.

Specific examples of the hydrocarbon oil (iv) include squalene, squalane, liquid paraffin, liquid isoparaffin, heavy liquid isoparaffin, an α-olefin oligomer, a cycloparaffin, polybutene, vaseline, a paraffin wax, a microcrystalline wax, a polyethylene wax, and ceresin. From the viewpoint of feeling of hair unification, squalane, squalene, liquid paraffin, and a paraffin wax are preferable; and one or more members selected among squalane, liquid paraffin, and a paraffin wax are more preferable.

From the same viewpoints as those described above, the higher alcohol (v) is preferably an alcohol having a linear or branched alkyl group or alkenyl group having a carbon number of 6 or more and not more than 22. The carbon number of the alkyl group or the alkenyl group is more preferably 8 or more and not more than 20, and still more preferably 12 or more and not more than 18.

Specific examples of the higher alcohol (v) include hexyl alcohol, 2-ethylhexyl alcohol, octyl alcohol, decyl alcohol, isodecyl alcohol, lauryl alcohol, myristyl alcohol, palmityl alcohol, cetyl alcohol, stearyl alcohol, isostearyl alcohol, 2-octyl dodecanol, eicosyl alcohol, and behenyl alcohol.

Of these, one or two or members selected among lauryl alcohol, myristyl alcohol, cetyl alcohol, stearyl alcohol, behenyl alcohol, and 2-octyl dodecanol are preferable.

From the same viewpoints as those described above, the carboxylic acid (vi) having a hydrocarbon group having a carbon number of from 17 to 23, which may be substituted with a hydroxyl group, is preferably a linear or branched alkyl group or alkenyl group.

Specific examples of the carboxylic acid having a hydrocarbon group having a carbon number of from 17 to 23, which may be substituted with a hydroxyl group, include stearic acid, oleic acid, isostearic acid, hydroxystearic acid, behenic acid, rhodinic acid, and the like. Of these, one or two or more members selected among stearic acid, oleic acid, isostearic acid, hydroxystearic acid, and behenic acid are preferable, and one or more members selected from oleic acid and isostearic acid are more preferable.

In the case where the surfactant composition according to the present invention is used as a hair cosmetic, from the viewpoint of, after treating the hair, obtaining a moist feeling and softness after drying, and in the case where the surfactant composition according to the present invention is used as a skin cleanser, from the viewpoint of obtaining an excellent moisturizing feeling after treating, rising and drying the skin, the content of the oil in the surfactant composition is preferably 0.01% by mass or more, more preferably 0.05% by mass or more, and still more preferably 0.1% by mass or more. From the viewpoint of suppressing a sticky feeling of the hair after treatment with a hair cosmetic and drying, the content of the oil in the surfactant composition is preferably not more than 30% by mass, more preferably not more than 20% by mass, and still more preferably not more than 15% by mass. In combining these viewpoints, the content of the oil is preferably from 0.01 to 30% by mass, more preferably from 0.05 to 20% by mass, and still more preferably from 0.1 to 15% by mass.

In the case where the hair cosmetic is a shampoo, from the same viewpoints as those described above, the content of the oil is yet still more preferably from 0.01 to 10% by mass, and even yet still more preferably from 0.1 to 8% by mass.

In the case where the hair cosmetic is a hair conditioner, from the same viewpoints as those described above, the content of the oil is yet still more preferably from 1 to 15% by mass, and even yet still more preferably from 3 to 12% by mass.

(Mass Ratio Between CGC and Surfactant)

From the viewpoint of in particular, after treating the hair, obtaining excellent smoothness and its long-lasting feeling at the time of rinsing and also the viewpoint of obtaining a moisturizing feeling after cleansing the skin, a content ratio between CGC and the surfactant in the surfactant composition according to the present invention is preferably 0.0002 or more, and more preferably 0.005 or more, and preferably not more than 10, more preferably not more than 5, and still more preferably not more than 3, in terms of a mass ratio of CGC to the surfactant [CGC/surfactant]. In addition, from the viewpoint of obtaining smoothness and its long-lasting feeling and moisturizing feeling as described above, the content ratio between CGC and the surfactant is preferably from 0.0002 to 10, more preferably from 0.0002 to 5, and still more preferably from 0.005 to 3.

In the case where the surfactant composition according to the present invention is used as a hair cosmetic and used as a shampoo, from the same viewpoints as those described above, the content ratio between CGC and the surfactant is preferably 0.005 or more, more preferably 0.01 or more, and still more preferably 0.02 or more, and preferably not more than 0.3, more preferably not more than 0.25, and still more preferably not more than 0.22, in terms of a mass ratio of CGC to the surfactant [CGC/surfactant]. In addition, from the same viewpoints as those described above, the content ratio between CGC and the surfactant is preferably from 0.005 to 0.3, more preferably from 0.01 to 0.25, and still more preferably from 0.02 to 0.22 in terms of a mass ratio of CGC to the surfactant [CGC/surfactant].

In the case where the surfactant composition according to the present invention is used as a hair cosmetic and used as a hair conditioner, from the same viewpoints as those described above, the content ratio between CGC and the surfactant is preferably 0.01 or more, more preferably 0.02 or more, and still more preferably 0.03 or more, and preferably not more than 3, more preferably not more than 1.5, and still more preferably not more than 1, and yet still more preferably not more than 0.7, in terms of a mass ratio of CGC to the surfactant [CGC/surfactant]. In addition, from the same viewpoints as those described above, the content ratio between CGC and the surfactant is preferably from 0.01 to 3, more preferably from 0.02 to 1.5, still more preferably from 0.03 to 1, and yet still more preferably from 0.03 to 0.7 in terms of a mass ratio of CGC to the surfactant [CGC/surfactant].

In the case where the surfactant composition according to the present invention contains an oil, from the same viewpoints as those described above, a mass ratio of CGC to the oil [CGC/oil] is preferably 0.01 or more and not more than 40.

In the case where the hair cosmetic is a shampoo, from the same viewpoints as those described above, the mass ratio [CGC/oil] is preferably 0.01 or more, more preferably 0.05 or more, and still more preferably 0.08 or more, and preferably not more than 30, more preferably not more than 10, and still more preferably not more than 5. From the same viewpoints as those described above, the mass ratio [CGC/ oil] in the case where the hair cosmetic is a shampoo is preferably from 0.01 to 30, more preferably from 0.05 to 10, and still more preferably from 0.08 to 5.

In the case where the hair cosmetic is a hair conditioner, from the same viewpoints as those described above, the mass ratio [CGC/oil] is preferably 0.005 or more, more preferably 0.01 or more, and still more preferably 0.02 or more, and preferably not more than 0.5, more preferably not more than 0.1, and still more preferably not more than 0.08. From the same viewpoints as those described above, the mass ratio [CGC/oil] in the case where the hair cosmetic is a hair conditioner is preferably from 0.005 to 0.5, more preferably from 0.01 to 0.1, and still more preferably from 0.02 to 0.08.

From the same viewpoints as those described above, a mass ratio of the surfactant to the oil [surfactant/oil] is preferably 0.01 or more, more preferably 0.05 or more, and still more preferably 0.1 or more, and preferably not more than 2,000, more preferably not more than 200, and still more preferably not more than 20. From the same viewpoints as those described above, the mass ratio [surfactant/oil] is preferably from 0.01 to 2,000, more preferably from 0.05 to 200, and still more preferably from 0.1 to 20.

In the case where the hair cosmetic is a shampoo, from the same viewpoints as those described above, the mass ratio [surfactant/oil] is preferably 0.5 or more, more preferably 1.5 or more, and still more preferably 3 or more, and preferably not more than 2,000, more preferably not more than 1,400, and still more preferably not more than 140. From the same viewpoints as those described above, the mass ratio [surfactant/oil] is preferably from 0.5 to 2,000, more preferably from 1.5 to 1,400, and still more preferably from 3 to 140.

In the case where the hair cosmetic is a hair conditioner, from the same viewpoints as those described above, the mass ratio [surfactant/oil] is preferably 0.01 or more, more preferably 0.02 or more, and still more preferably 0.05 or more, and preferably not more than 2, more preferably not more than 1.0, and still more preferably not more than 0.5. From the same viewpoints as those described above, the mass ratio [surfactant/oil] is preferably from 0.01 to 2, more preferably from 0.02 to 1.0, and still more preferably from 0.05 to 0.5.

(Other Components)

The surfactant composition according to the present invention can be further properly blended with glycerin, a humectant, a polysaccharide, a polypeptide, a pearlescent agent, a solvent, a pigment, a perfume, a propellant, chelating agent such as ethylenediaminetetraacetic acid salts, citric acid salts, etc., a pH regulator, an antiseptic, an anti-dandruff agent such as zinc pyrithione, piroctone olamine, etc., and the like, which are usually blended in hair cosmetics or skin cleansers, as the need arises.

(Manufacturing Method of Surfactant Composition)

A manufacturing method of the surfactant composition according to the present invention is not particularly limited, and the surfactant composition can be manufactured in the usual way. Specifically, for example, in the case of a liquid hair shampoo, water and a surfactant are heated and uniformly mixed. After confirming uniform dissolution, CGC is added and mixed. If desired, CGC can be added after being dispersed or dissolved in water in advance. After adding CGC to the surfactant aqueous solution, the contents are uniformly dissolved or dispersed and then cooled, to which are then added a pearlescent agent, a pH regulator, a perfume, a pigment, and the like, as the need arises. Thus, the surfactant composition can be prepared.

In addition, in the case where the surfactant composition contains an oil, for example, in the case of a liquid hair shampoo, there are exemplified (i) a method in which after heating water and a surfactant and uniformly mixing them, CGC is added and mixed, to which is then added an oil, and the contents are uniformly dissolved or emulsified; (ii) a method in which after uniformly dissolving CGC in water, a surfactant is added at a temperature of ordinary temperature or higher, to which is then added an oil, and the contents are uniformly dissolved or emulsified; and the like. After uniformly dissolving or dispersing the oil, the contents are cooled, and a pearlescent agent, a pH regulator, a perfume, a pigment, and the like are then added, as the need arises. Thus, the surfactant composition can be prepared.

In addition, a formulation of the surfactant composition according to the present invention is not particularly limited, and arbitrary formulations such as a liquid form, a foam form, a paste form, a cream form, a solid form, a powder form, etc. can be adopted. Of these, a liquid form, a paste film, and a cream form are preferable, and a liquid form is especially preferable. In the case of a liquid form, it is preferable to use, as a liquid medium, polyethylene glycol, ethanol, or the like, in addition to water. A blending amount of water is preferably 10% by mass or more and not more than 90% by mass in the whole of the composition.

In accordance with the surfactant composition according to the present invention, after treating the hair, it is possible to impart excellent smoothness and its long-lasting feeling at the time of rinsing and a moist feeling and softness after drying, and after cleansing the skin with the surfactant composition, rinsing, and drying, it is possible to give an excellent moisturizing feeling to the skin. Therefore, the surfactant composition according to the present invention can be suitably used as a hair cosmetic or a skin cleanser.

Specific examples of the hair cosmetic include a hair shampoo, a hair rinse, a hair treatment, a hair conditioner, a leave-in type hair conditioner, a hair cream, a blow lotion, a hair pack, a hair color, a hair-perm agent, a conditioning gel, a conditioning foam, and the like. Of these, taking into consideration the above-described effects by the surfactant composition according to the present invention, the hair cosmetic is preferably used for a hair shampoo, a hair rinse, a hair treatment, a hair conditioner, a leave-in type hair conditioner, a hair cream, a hair pack, a hair color, or a hair-perm agent, and the hair cosmetic is more preferably used for a hair shampoo, a hair rinse, a hair treatment, or a hair conditioner.

In addition, specific examples of the skin cleanser include a body soap, a hand wash, a face wash, and a makeup remover. Of these, taking into consideration the above-described effects by the surfactant composition according to the present invention, the skin cleanser is preferably used for a body soap, a hand wash, or a face wash.

[Hair Cosmetic Composition and Skin Cleanser Composition]

The hair cosmetic composition and the skin cleanser composition according to the present invention contain CGC according to the present invention, a surfactant, and water. CGC and the surfactant which are contained in the hair cosmetic composition and the skin cleanser composition and preferred modes thereof are the same as those in the above-described surfactant composition, and as the hair cosmetic composition and the skin cleanser composition according to the present invention, the above-described surfactant composition according to the present invention may be used as it is.

As for the above-described embodiments, the present invention discloses the following cationized glycerolated cellulose, surfactant composition, utilization of the surfactant composition, hair cosmetic composition, and skin cleanser composition.

<1>

A cationized glycerolated cellulose having a main chain derived from an anhydroglucose represented by the foregoing general formula (1), wherein a degree of substitution of a cationized alkylene oxy group per the anhydroglucose unit is from 0.01 to 0.18, and a degree of substitution of a glycerol group per the anhydroglucose unit is from 0.5 to 5.0.

(In the foregoing general formula (1), each of $R^1$, $R^2$, and $R^3$ independently indicates a substituent composed of one or more repeating units selected among the foregoing formulae (2) to (5), or a hydrogen atom, provided that all of $R^1$, $R^2$, and $R^3$ in the molecule are not a hydrogen atom at the same time; and n indicates an average polymerization degree of the main chain derived from an anhydroglucose and is a number of from 100 to 12,000.)

(In the foregoing formulae (2) to (5), a repeating unit structure represented by the formula (2) or (3) indicates a cationized alkylene oxy group; a repeating unit structure represented by the formula (4) or (5) indicates a glycerol group; each of $R^4$ to $R^9$ independently indicates a linear or branched alkyl group having a carbon number of from 1 to 3; $X^-$ and $Y^-$ indicate an anion; r and s indicate an integer of from 0 to 3; and in the repeating unit structures represented by the formulae (2) to (5), the oxygen atom is bound to a hydrogen atom or a carbon atom of other repeating unit.)

<2>

The cationized glycerolated cellulose as set forth above in <1>, wherein the degree of substitution of a cationized alkylene oxy group per the anhydroglucose unit is 0.03 or more, preferably 0.06 or more, more preferably 0.08 or more, and still more preferably 0.1 or more, and preferably not more than 0.17, more preferably not more than 0.16, and still more preferably not more than 0.15, and is also from 0.03 to 0.17, preferably from 0.06 to 0.16, more preferably from 0.08 to 0.15, and still more preferably from 0.1 to 0.15.

<3>

The cationized glycerolated cellulose as set forth above in <1> or <2>, wherein the degree of substitution of a glycerol group per the anhydroglucose unit is 0.6 or more, preferably 0.8 or more, and more preferably 1.0 or more, and not more than 4.0, preferably not more than 3.0, more preferably not more than 2.5, and still more preferably not more than 2.0, and is also from 0.6 to 3.0, preferably from 0.8 to 2.5, and more preferably from 1.0 to 2.0.

<4>

The cationized glycerolated cellulose as set forth above in any one of <1> to <3>, wherein an average polymerization degree n of the main chain derived from the anhydroglucose is 200 or more, preferably 500 or more, and more preferably 1,000 or more, and not more than 10,000, preferably not more than 5,000, and more preferably not more than 2,500, and is also from 200 to 10,000, preferably from 500 to 5,000, and more preferably from 1,000 to 2,500.

<5>

The cationized glycerolated cellulose as set forth above in any one of <1> to <4>, wherein in the formulae (2) and (3), each of $R^4$ to $R^9$ is independently a methyl group or an ethyl group, and preferably a methyl group.

<6>

The cationized glycerolated cellulose as set forth above in any one of <1> to <5>, wherein in the formulae (2) and (3), $X^-$ and $Y^-$ are one or more members selected among an alkyl sulfate ion (having a carbon number of 1 or more and not more than 3), a sulfuric acid ion, and a halide ion, preferably a halide ion, and more preferably a chloride ion.

<7>

The cationized glycerolated cellulose as set forth above in any one of <1> to <6>, wherein in the formulae (2) and (3), each of r and s is 1.

<8>

The cationized glycerolated cellulose as set forth above in any one of <1> to <7>, wherein a cation charge density is 0.05 mmol/g or more, preferably 0.1 mmol/g or more, more preferably 0.2 mmol/g or more, still more preferably 0.25 mmol/g or more, and yet still more preferably 0.3 mmol/g or more, and not more than 0.8 mmol/g, preferably not more than 0.7 mmol/g, more preferably not more than 0.6 mmol/g, and still more preferably not more than 0.5 mmol/g, and is also from 0.05 to 0.8 mmol/g, preferably from 0.1 to 0.7 mmol/g, more preferably from 0.2 to 0.6 mmol/g, still more preferably from 0.25 to 0.6 mmol/g, and yet still more preferably from 0.3 to 0.5 mmol/g.

<9>

The cationized glycerolated cellulose as set forth above in any one of <1> to <8>, wherein a viscosity of a 1% by mass aqueous solution at 25° C. is 1 mPa·s or more, preferably 10 mPa·s or more, and more preferably 20 mPa·s, and not more than 100,000 mPa·s, preferably not more than 10,000 mPa·s, and more preferably not more than 6,000 mPa·s, and is also from 1 to 100,000 mPa·s, preferably from 10 to 10,000 mPa·s, and more preferably from 20 to 6,000 mPa·s.

<10>

The cationized glycerolated cellulose as set forth above in any one of <1> to <9>, wherein a degree of substitution of a hydrocarbon group having a carbon number of 7 or more per the anhydroglucose unit is less than 0.01, preferably not more than 0.005, more preferably not more than 0.001, and still more preferably 0.

<11>

A surfactant composition containing the cationized glycerolated cellulose as set forth above in any one of <1> to <10>, a surfactant, and water.

<12>

The surfactant composition as set forth above in <11>, wherein the content of the cationized glycerolated cellulose is 0.01% by mass or more, preferably 0.05% by mass or more, and more preferably 0.1% by mass or more, and not more than 10% by mass, preferably not more than 5% by mass, and more preferably not more than 1% by mass, and is also from 0.01 to 10% by mass, preferably from 0.05 to 5% by mass, and more preferably from 0.1 to 1% by mass.

<13>

The surfactant composition as set forth above in <11> or <12>, wherein a mass ratio of the cationized glycerolated cellulose to the surfactant [(cationized glycerolated cellulose)/(surfactant)] is 0.0002 or more, and preferably 0.005 or more, and not more than 10, preferably not more than 5, and more preferably not more than 3, and is also from 0.0002 to 10, preferably from 0.0002 to 5, and more preferably from 0.005 to 3.

<14>

The surfactant composition as set forth above in any one of <11> to <13>, wherein the content of the surfactant is 0.1% by mass or more, preferably 0.5% by mass or more, more preferably 1% by mass or more, and still more preferably 5% by mass or more, and not more than 80% by mass, preferably not more than 50% by mass, and more preferably not more than 36% by mass, and is also from 0.1 to 80% by mass, preferably from 0.5 to 50% by mass, and more preferably from 1 to 36% by mass.

<15>

The surfactant composition as set forth above in any one of <11> to <14>, wherein the surfactant is at least one selected from anionic surfactants selected among alkyl sulfates, polyoxyethylene alkyl ether sulfates, polyoxyethylene alkyl ether acetates, alkyl sulfosuccinates, acyl glutamates, acyl isethionates, and acyl methyl taurates; nonionic surfactants selected among polyoxyalkylene alkyl ethers, polyoxyethylene hydrogenated castor oils, fatty acid alkanolamides, and alkyl glucosides; and ampholytic surfactants selected among alkyldimethylamino acetic acid betaines, fatty acid amidopropyl betaines, and alkylhydroxy sulfobetaines.

<16>

The surfactant composition as set forth above in any one of <11> to <15>, further containing an oil.

<17>

The surfactant composition as set forth above in <16>, wherein the content of the oil is 0.01% by mass or more, preferably 0.05% by mass or more, and more preferably 0.1% by mass or more, and not more than 30% by mass, preferably not more than 20% by mass, and more preferably not more than 15% by mass, and is also from 0.01 to 30% by mass, preferably from 0.05 to 20% by mass, and more preferably from 0.1 to 15% by mass.

<18>

The surfactant composition as set forth above in <16> or <17>, wherein the oil is one or two or more members selected among an ester oil, a silicone oil, an ether oil, a hydrocarbon oil, a higher alcohol, and a carboxylic acid having a hydrocarbon group having a carbon number of from 17 to 23 which may be substituted with a hydroxyl group.

<19>

A use of the cationized glycerolated cellulose as set forth above in any one of <1> to <10> for a hair cosmetic composition.

<20>

A use of the cationized glycerolated cellulose as set forth above in any one of <1> to <10> for a skin cleanser composition.

<21>

A use of the surfactant composition as set forth above in any one of <11> to <18> as a hair cosmetic composition.

<22>

A use of the surfactant composition as set forth above in any one of <11> to <18> as a skin cleanser composition.

<23>

A hair cosmetic composition containing the cationized glycerolated cellulose as set forth above in any one of <1> to <10>, a surfactant, and water.

<24>

The hair cosmetic composition as set forth above in <23>, further containing an oil.

<25>

The hair cosmetic composition as set forth above in <24>, wherein the content of the oil is 0.01% by mass or more, preferably 0.05% by mass or more, and more preferably 0.1% by mass or more, and not more than 30% by mass, preferably not more than 20% by mass, and more preferably not more than 15% by mass, and is also from 0.01 to 30% by mass, preferably from 0.05 to 20% by mass, and more preferably from 0.1 to 15% by mass.

<26>

The hair cosmetic composition as set forth above in <24> or <25>, wherein the oil is one or two or more members selected among an ester oil, a silicone oil, an ether oil, a hydrocarbon oil, a higher alcohol, and a carboxylic acid having a hydrocarbon group having a carbon number of from 17 to 23, which may be substituted with a hydroxyl group.

<27>

The use of the composition as set forth above in any one of <23> to <26> as a hair cosmetic for imparting smoothness and a long-lasting feeling at the time of rinsing the hair and a moist feeling and softness to the hair after drying.

<28>

A skin cleanser composition containing the cationized glycerolated cellulose as set forth above in any one of <1> to <10>, a surfactant, and water.

<29>

The skin cleanser composition as set forth above in <28>, further containing an oil.

<30>

The skin cleanser composition as set forth above in <29>, wherein the content of the oil is 0.01% by mass or more, preferably 0.05% by mass or more, and more preferably 0.1% by mass or more, and not more than 30% by mass, preferably not more than 20% by mass, and more preferably not more than 15% by mass, and is also from 0.01 to 30% by mass, preferably from 0.05 to 20% by mass, and more preferably from 0.1 to 15% by mass.

<31>

The skin cleanser composition as set forth above in <29> or <30>, wherein the oil is one or two or more members selected among an ester oil, a silicone oil, an ether oil, a hydrocarbon oil, a higher alcohol, and a carboxylic acid having a hydrocarbon group having a carbon number of from 17 to 23, which may be substituted with a hydroxyl group.

<32>

The use of the composition as set forth above in any one of <28> to <31> as a skin cleanser for imparting a moisturizing feeling to the skin after drying.

<33>

A method for manufacturing the cationized glycerolated cellulose as set forth above in any one of <1> to <10>, comprising, after undergoing the following steps (1) and (2), carrying out cationization and glycerolation.

Step (1): A step of pulverizing a raw material cellulose in the presence of an alkali compound in an amount of 0.6 molar equivalents or more and not more than 1.5 molar equivalents to one mole of an anhydroglucose unit of the raw material cellulose and also in the presence of water in an amount of not more than 10% by mass relative to the raw material cellulose, thereby obtaining a cellulose powder mixture.

Step (2): A step of adding water to the cellulose powder mixture obtained in the step (1) to adjust the water content in the cellulose powder mixture at 30% by mass or more and not more than 100% by mass relative to the raw material cellulose used in the step (1), thereby obtaining a powdered alkali cellulose.

EXAMPLES

In the following Manufacturing Examples, Examples, and Comparative Examples, "%" means "% by mass". Incidentally, various physical properties and the like were measured in the following methods.

(1) Measurement of Viscosity Average Polymerization Degree of Each of Cellulose and CGC (Cuprous Ammoniacal Process):
(i) Preparation of Solution for Measurement:
In a volumetric flask (100 mL), 0.5 g of cuprous chloride and 20 to 30 mL of 25% ammonia water were charged and completely dissolved. Thereafter, 1.0 g of cupric hydroxide and 25% ammonia water were added until the bottom of the meniscus of the liquid reached an upper edge of the marked line of the volumetric flask, and the contents were stirred for 3 hours and completely dissolved.
(ii) Preparation of Sample:
In a volumetric flask (25 mL), 25 mg of a measurement sample was charged, and the solution prepared above was then added until the bottom of the meniscus of the liquid reached an upper edge of the marked line of the volumetric flask. The contents were stirred for 6 hours and completely dissolved.
(iii) Measurement of Viscosity Average Polymerization Degree:
In a Ubbelohde viscometer, the obtained cuprammonium aqueous solution was charged and allowed to stand in a constant temperature tank (20±0.1° C.) for one minute, and a flow rate of the liquid was then measured. A relative viscosity $\eta_r$ expressed by the following equation was determined from a flow time (t (sec)) of the cuprammonium solution in various sample concentrations (g/L) and a flow time ($t_0$ (sec)) of a cuprammonium aqueous solution to which no sample had been added.

$$\eta_r = t/t_0$$

Next, a reduced viscosity ($\eta_{sp}/c$) in each concentration was determined according to the following equation.

$$\eta_{sp}/c = (\eta_r - 1)/c \ (c: \text{sample concentration(g/dL)})$$

Furthermore, the reduced viscosity was extrapolated at c=0 to determine an intrinsic viscosity [η], and a viscosity average polymerization degree (n) was determined according to the following equation.

$$n = 2000 \times [\eta]$$

(2) Calculation of Degree of Substitution: MS of CGC:
A degree of substitution (MS(N+)) of a cationized alkylene oxy group and a degree of substitution (MS(Gly)) of a glycerol group were calculated according to the following simultaneous equations.

(74.1−74.1×(content of glycerol group(% by mass)))×MS(Gly)−a×(content of glycerol group(% by mass))×MS(N+)=162.1×(content of glycerol group(% by mass))

(−74.1×(nitrogen content(% by mass)))×MS(Gly)+ (14−a×(nitrogen content(% by mass)))× MS(N+)=162.1×(nitrogen content(% by mass))

(In the equations, "a" indicates a molecular weight of the cationized alkylene oxy group and is 151.6 in the following Examples.)

In the foregoing simultaneous equations, the nitrogen content (% by mass) and the content of glycerol group (% by mass) indicate % by mass of nitrogen and the glycerol group constituting the cationized alkylene oxy group contained in CGC, respectively and were calculated in the following methods.
[Content % of Glycerol Group]
The content % (% by mass) of the glycerol group contained in CGC was calculated in conformity with the Zeisel method which is known as a technique for analyzing an average addition mole number of an alkoxy group of cellulose ether, as described in *Analytical Chemistry*, Vol. 51, No. 13, 2172 (1979), *The Japanese Pharmacopoeia Fifteenth Edition* (Section of Analysis Method of Hydroxypropylcellulose), and the like. The procedures are hereunder shown.

(i) In a 25-mL volumetric flask, 1 mL of n-octane was charged, and o-xylene was added until the bottom of the meniscus of the liquid reached an upper edge of the marked line of the volumetric flask, and the contents were stirred, thereby preparing an internal standard solution.

(ii) 65 mg of CGC as purified and dried and 65 mg of adipic acid were precisely weighed in a 10-mL vial, and 2 mL of the internal standard solution prepared in (i) and 2 mL of hydroiodic acid were added, followed by sealing hermetically.

(iii) The mixture in the vial was heated by a block heater at 150° C. for one hour while stirring with a stirrer chip.

(iv) An upper layer (o-xylene layer) of the mixture as separated into two phases in the vial was analyzed by means of gas chromatography. The analysis condition was as follows.

Column: Chromosorb WAW DMCS, 60 to 80 mesh
Column temperature: 60° C. (5 min)→10° C./min→300° C. (10 min)
Injector temperature: 250° C.
Detector temperature: 250° C.
Implanted amount: 1 μL The content (% by mass) of the glycerol group in CGC was calculated from the detected amount of isopropyl iodide.
[Measurement of Nitrogen Content (% by Mass)] (Kjeldahl Method)
100 mg of CGC as purified and dried was precisely weighed, to which were then added 10 mL of sulfuric acid and one tablet of a decomposition promoter (KJELTABS tablet, available from Nakayama Rika Seisakusho K.K.), and the contents were completely decomposed while successively heating at 250° C. for 30 minutes, at 300° C. for 30 minutes, and at 420° C. for 80 minutes using a Kjeldahl decomposition apparatus (K-432, available from BUCHI). After completion of the decomposition reaction, 30 mL of ion-exchanged water was added to the sample, and 40 mL of a 30% sodium hydroxide aqueous solution was added using an automatic Kjeldahl distillation/titration apparatus (K-370, available from BUCHI), thereby rendering the sample alkaline. Liberated ammonia was then collected into a 1% boric acid aqueous solution by a distillation operation and titrated with 0.01 N sulfuric acid (for quantitative analysis, available from Wako Pure Chemical Industries, Ltd.), thereby determining the nitrogen content (% by mass) in CGC.

(3) Measurement of Degree of Direct Substitution: DS:
DS(N+) of the cationized alkylene oxy group or DS(Gly) of the glycerol group was calculated in the following manner. That is, the $^{13}$C-NMR measurement was carried out, and the calculation was made according to the following equation by using the obtained results and the assignment described in *Macromol. Chem.*, Vol. 193, P 647-658 (1992), or the like.

$$DS = \frac{I_{C1S} + I_{C3S} + (I_{C1+C1S} - I_{C6})}{I_{C1+C1S}}$$

(In the equation, $I_{C1}$ indicates a peak intensity of the unsubstituted carbon atom at the 1-position of the glucose residue; $I_{C1S}$ indicates a peak intensity of the substituted carbon atom at the 1-position of the glucose residue; $I_{C3S}$ indicates a peak intensity of the substituted carbon atom at the 3-position of the glucose residue; and $I_{C6}$ indicates a peak intensity of the unsubstituted carbon atom at the 6-position of the glucose residue.)

(i) Case of CGC Obtained by Allowing Cellulose and a Glycerolating Agent to React with Each Other to Obtain a Glycerolated Cellulose, Followed by Reacting with a Cationizing Agent:

A part of the glycerolated cellulose that is an intermediate and CGC were purified and dried, and then subjected to the $^{13}$C-NMR measurement, and DS of each of them was calculated using the foregoing equation.

In the case where the measurement sample is the glycerolated cellulose as an intermediate, the obtained DS is DS(Gly) of the glycerolated cellulose as an intermediate. This value was equated with DS(Gly) of CGC obtained by allowing the subject intermediate to further react with a cationizing agent.

In the case where the measurement sample is CGC, the obtained DS is a sum of DS(Gly) and DC(N+) of CGC. Therefore, a difference between this value and the value of DS(Gly) of the above-described glycerolated cellulose as an intermediate was defined as DS(N+) of the obtained CGC.

(ii) Case of CGC Obtained by Allowing Cellulose and a Cationizing Agent to React with Each Other to Obtain a Cationized Cellulose, Followed by Reacting with a Glycerolating Agent:

A part of the cationized cellulose that is an intermediate and CGC were purified and dried, and then subjected to the $^{13}$C-NMR measurement, and DS of each of them was calculated using the foregoing equation.

In the case where the measurement sample is the cationized cellulose as an intermediate, the obtained DS is DS(N+) of the cationized cellulose as an intermediate. This value was equated with DS(N+) of CGC obtained by allowing the subject intermediate to further react with a glycerolating agent.

A difference of the obtained DS relative to CGC from the value of DS(N+) of the above-described cationized cellulose as an intermediate was defined as DS(Gly) of the obtained CGC.

(4) Measurement of Aqueous Solution Viscosity of CGC:

In a 50-mL vial, 0.5 g of a solid of CGC as purified and dried and 49.5 g of ion-exchanged water were charged and dissolved with stirring over 6 hours, thereby preparing a 1% by mass aqueous solution. The obtained 1% by mass aqueous solution was adjusted to 25° C. in a constant-temperature water tank, and a viscosity of the 1% by mass aqueous solution was measured using a B type viscometer (TVB-10M, available from Toki Sangyo Co., Ltd.) under conditions of measurement temperature: 25° C., rotation number: 30 rpm, and rotor: No. 1, 2, 3, or 4.

In choosing the rotor used, a rotor in which the measurement result falls within the range of from 20 to 90% of an upper limit value within the measurement range of the viscosity relative to the rotor used was chosen and provided for the measurement.

(5) Measurement of Water Content:

The water content of a pulp or powdered cellulose was measured using an electronic moisture analyzer "MOC-120H" (available from Shimadzu Corporation). About 1 g of a sample was used, and a point at which a weight change rate at a measurement temperature of 120° C. for 30 seconds became not more than 0.1% was defined as an end point of the measurement.

Example 1

Manufacture of CGC (1)

(1) Powdering Step of Cellulose:

A wood pulp in a sheet form (BIOFLOC HV+, available from Tembec, average polymerization degree: 1,550) was put in a shredder (MSX2000-IVP440F, available from Meiko Shokai Co., Ltd.) to form chips. Thereafter, the chips were subjected to a drying treatment at 80° C. under reduced pressure for 12 hours, thereby obtaining a dry pulp in a chip form having a water content of 0.8%.

Subsequently, 920 g of the obtained dry pulp in a chip form and 227.2 g of sodium hydroxide in a granular form (1.0 molar equivalent/AGU, available from Kishida Chemical Co., Ltd., special grade reagent) were thrown into a batch type vibration mill (FV-10, available from Chuo Kakohki Co., Ltd., total volume of container: 33 L; 63 SUS304-made rods of ϕ30 mm and 510 mm in length and having a circular cross-sectional shape were used as the rod). The contents were pulverized at a vibration number of 20 Hz and a total amplitude of 8 mm and at a temperature ranging from 10 to 40° C. for 10 minutes, thereby obtaining 1,140 g of a mixed powder of cellulose and alkali.

(2) Glycerolation Reaction:

To 62.3 g of the mixed powder of cellulose and alkali obtained above, 15 g (30% per cellulose) of ion-exchanged water was added by means of spraying, followed by mixing using a mortar. This mixture was charged in a 1-L kneader equipped with a reflux tube (PNV-1 Model, available from Irie Shokai Co., Ltd.), and warm water was flown with a jacket in a nitrogen atmosphere while stirring, thereby adjusting a jacket temperature to 50° C. Subsequently, a solution obtained by diluting 18.3 g (0.8 moles/AGU) of glycidol (available from Kanto Chemical Co., Inc.) as a glycerolating agent with 37.2 g of tetrahydrofuran (concentration of glycerolating agent: 33%) was added dropwise over 30 minutes, and the contents were stirred at a jacket temperature of 50° C. for 3 hours.

(3) Cationization Reaction:

Subsequently, 7.15 g (0.08 mmol/AGU) of HAC-65 (a 65% 3-chloro-2-hydroxypropyltrimethylammonium chloride aqueous solution (available from Yokkaichi Chemical Company, Limited)) as a cationizing agent was added dropwise to the mixture obtained by the glycerolation reaction over 20 minutes, and the contents were stirred at a jacket temperature of 50° C. for 3 hours. Thereafter, water at 20° C. was flown into the jacket, and the resultant was stirred for 30 minutes and then cooled, thereby obtaining 125 g of a pale yellow powder.

(4) Neutralization and Purification Step:

5.0 g of the obtained pale yellow powder was dissolved in ion-exchanged water to prepare a 1% aqueous solution; the alkali was then neutralized with acetic acid; and the resultant was purified by means of dialysis with ion-exchanged water using a dialysis membrane (a trade name: SPECTRAPORE 6, available from Wako Pure Chemical Industries, Ltd., cutoff molecular weight: 8,000). Specifically, 500 g of the foregoing 1% aqueous solution was enclosed in the dialysis membrane, which was then dipped in ion-exchanged water in an amount of 20 times by mass or more relative to the foregoing 1% aqueous solution, and the water outside the dialysis membrane was exchanged with ion-exchanged water three times every time the dialysis membrane was allowed to stand for at least 3 hours, followed by allowing the resulting dialysis membrane to stand for 3 hours or more. After completion of dialysis purification, the resultant was freeze-dried to obtain 3.1 g of CGC as a white solid. Subsequently, a 1% aqueous solution of the obtained CGC was prepared and centrifuged at 3,000 rpm (2,000×g) for 20 minutes using a centrifuge (a product name: table top type centrifuge, H-28F, available from Kokusan Co., Ltd.), thereby precipitating an insoluble matter. A supernatant of this aqueous solution was freeze-dried using a freeze dryer (FDU-1100, available from EYELA), thereby obtaining CGC (1).

As a result of analysis of the obtained CGC (1), the content of glycerol group was 38.0%, and the nitrogen content was 0.21%. The degree of substitution of glycerol group (MS(Gly)) and the degree of substitution of cationized propylene oxy group (MS (N+)) were 1.39 and 0.04, respectively. The results are shown in Table 1.

Examples 2 to 9

Manufacture of CGC (2) to CGC (9)

CGC (2) to CGC (9) were obtained in the same manner as that in Example 1, except for changing the addition amounts of the glycerolating agent (glycidol) and the cationizing agent (HAC-65). As for CGC (7), the degree of direct substitution of cationized propylene oxy group (DS(N+)) was also measured, and as for CGC (8), DS(N+) and the degree of direct substitution of glycerol group (DS(Gly)) were also measured.

The results are shown in Tables 1 and 2.

Example 10

Manufacture of CGC (10)

CGC was manufactured by changing the addition order of the glycerolating agent and the cationizing agent.
(1) Powdering Step of Cellulose:
The same operation as that in Example 1 was followed to obtain a mixed powder of cellulose and alkali.
(2) Cationization Reaction:
To 62.3 g of the obtained mixed powder of cellulose and alkali, 15 g (30% per cellulose) of ion-exchanged water was added by means of spraying, followed by mixing using a mortar. This mixture was charged in a 1-L kneader equipped with a reflux tube (PNV-1 Model, available from Irie Shokai Co., Ltd.), and warm water was flown into a jacket in a nitrogen atmosphere while stirring, thereby adjusting a jacket temperature to 50° C. Subsequently, 14.3 g (0.16 moles/AGU) of HAC-65 used in Example 1 as a cationizing agent was added dropwise over 30 minutes. Thereafter, the contents were stirred at a jacket temperature of 50° C. for 5 hours. DS(N+) was 0.12.
(3) Glycerolation Reaction:
Subsequently, a solution obtained by diluting 29.7 g (1.3 moles/AGU) of glycidol as a glycerolating agent with 60.3 g of tetrahydrofuran (concentration of glycerolating agent: 330) was added dropwise to the mixture obtained by the cationization reaction over 30 minutes. Thereafter, the contents were stirred at a jacket temperature of 50° C. for 3 hours. Thereafter, water at 20° C. was flown into the jacket, and the resultant was stirred for 30 minutes and then cooled, thereby obtaining 130 g of a pale yellow powder.
(4) Neutralization and Purification Step:
5.0 g of the obtained pale yellow powder was subjected to the same neutralization and purification operation as that in Example 1, thereby obtaining CGC (10).

As a result of analysis of the obtained CGC (10), the content of glycerol group was 33.90, and the nitrogen content was 0.62%. MS(Gly) and MS (N+) were 1.25 and 0.12, respectively, and DS(Gly) was 0.83. The results are shown in Tables 1 and 2.

Example 11

Manufacture of CGC (11)

Cellulose was uniformly dissolved in a solvent and allowed to react with a glycerolating agent and a cationizing agent to manufacture CGC.
(1) Powdering Step of Cellulose:
A wood pulp in a sheet form (BIOFLOC HV+, available from Tembec, average polymerization degree: 1,550) was put in a shredder (MSX2000-IVP440F, available from Meiko Shokai Co., Ltd.) to form chips. Thereafter, the chips were subjected to a drying treatment at 80° C. under reduced pressure for 12 hours, thereby obtaining a dry pulp in a chip form having a water content of 0.8%.

Subsequently, 920 g of the obtained dry pulp in a chip form was thrown into a batch type vibration mill (FV-10, available from Chuo Kakohki Co., Ltd., total volume of container: 33 L; 63 SUS304-made rods of φ30 mm and 510 mm in length and having a circular cross-sectional shape were used as the rod). The pulp was pulverized at a vibration number of 20 Hz and a total amplitude of 8 mm and at a temperature ranging from 10 to 40° C. for 10 minutes, thereby obtaining 890 g of a cellulose powder.
(2) Glycerolation Reaction:
In a three-necked round bottom flask, 389.2 g of dimethyl sulfoxide (DMSO, available from Wako Pure Chemical Industries, Ltd.) and 77.5 g of tetra (n-butyl) ammonium fluoride trihydrate (TBAF, available from Kanto Chemical Co., Inc.) were thrown and uniformly dissolved. 7.0 g of the cellulose powder obtained above was added thereto, and the contents were stirred and dissolved at room temperature for one hour. Furthermore, 2.42 g (1.0 molar equivalent/AGU) of finely powdered potassium hydroxide was added, and the contents were well dispersed. After increasing the temperature to 70° C., 51.2 g of a 50% dimethyl sulfoxide solution of 25.6 g (8.0 moles/AGU) of glycidol was added in a nitrogen gas stream over 5 hours while stirring the reaction solution. After completion of the dropwise addition, stirring was further continued at 70° C. for one hour, thereby completing the reaction.

Subsequently, after cooling the reaction solution to room temperature, the resultant was centrifuged, and the obtained supernatant was thrown into a mixed solvent of ion-exchanged water/acetone/methanol=2/4/4 (volume ratio), and a deposited polymer was recovered and dried under reduced pressure to obtain 8.82 g of a glycerolated cellulose as a white solid. DS(Gly) was 1.23.
(3) Cationization Reaction:
In a three-necked round bottom flask, 166.7 g of a 50% dimethyl sulfoxide aqueous solution was thrown, 2.5 g of the glycerolated cellulose obtained above was added, and the contents were stirred and uniformly dissolved at room temperature. Thereafter, 0.4 g (0.2 molar equivalents/AGU) of a 20% sodium hydroxide aqueous solution was added, followed by stirring at room temperature. Thereafter, 1.46 g (0.8 molar equivalents/AGU) of glycidyltrimethylammonium chloride (available from Sakamoto Yakuhin Kogyo Co., Ltd., water content: 20% by mass, purity: 90% or more) as a cationizing agent was added with stirring, and the temperature was then increased to 50° C., followed by reaction for 5 hours. Thereafter, the reaction solution was neutralized with acetic acid, the resultant was thrown into ethanol, and a deposited polymer was recovered and dried under reduced pressure to obtain 1.9 g of CGC (11) as a white solid.

As a result of analyzing a degree of substitution of the obtained CGC (11), the content of glycerol group was 34.6%. In addition, the nitrogen content was 0.70%. MS(Gly) and MS (N+) were 1.31 and 0.14, respectively. The results are shown in Tables 1 and 2.

Example 12

Manufacture of CGC (12)

The same procedures as those in Example 11 were followed, except for changing the sheet wood pulp as the cellulose raw material to a cotton linter pulp (average polymerization degree: 2,005).

As a result of analyzing the obtained CGC (12), the content of glycerol group was 33.4%, and the nitrogen content was 0.43%. MS(Gly) and MS (N+) were 1.18 and 0.08, respectively. The results are shown in Tables 1 and 2.

Examples 13 to 14

Manufacture of CGC (15) to CGC (16)

CGC (15) to CGC (16) were obtained in the same manner as that in Example 1, except for changing the addition amounts of the glycerolating agent (glycidol) and the cationizing agent (HAC-65). The results are shown in Table 1.

Example 15

Manufacture of CGC (17)

CGC (17) was obtained in the same manner as that in Example 7, except for changing the addition amounts of the glycerolating agent (glycidol) and the cationizing agent (HAC-65).

As a result of analyzing the obtained CGC (17), the content of glycerol group was 38.9%, and the nitrogen content was 0.61%. The degree of substitution of glycerol group and the degree of substitution of cationized alkylene oxy group were 1.56 and 0.13, respectively. The results are shown in Table 1.

Example 16

Manufacture of CGC (18)

2.2 g of CGC (18) was obtained in the same manner as that in Example 11, except for changing the addition amounts of the glycerolating agent (glycidol) and the cationizing agent (glycidyltrimethylammonium chloride).

As a result of analyzing the obtained CGC (18), the content of glycerol group was 36.0%, and the nitrogen content was 0.36%. The degree of substitution of glycerol group and the degree of substitution of cationized alkylene oxy group were 1.31 and 0.07, respectively. The results are shown in Table 1.

Example 17

Manufacture of CGC (19)

CGC (19) was obtained in the same manner as that in Example 11, except for changing the addition amounts of the glycerolating agent (glycidol) and the cationizing agent (glycidyltrimethylammonium chloride) and changing the sheet wood pulp as the cellulose raw material to a cotton linter pulp (average polymerization degree: 2,005). The results are shown in Table 1.

Comparative Examples 1 to 2

Manufacture of CGC (13) to CGC (14)

CGC (13) to CGC (14) were obtained in the same manner as that in Example 1, except for changing the addition amounts of the glycerolating agent (glycidol) and the cationizing agent (HAC-65). The results are shown in Table 1.

Comparative Example 3

Manufacture of Glycerolated Cellulose, GC (1)

Cellulose having been subjected to glycerolation (glycerolated cellulose (hereinafter also referred to as "GC")) was manufactured without carrying out the cationization reaction.

(1) Powdering Step of Cellulose:
The same operation as that in Example 1 was followed to obtain a mixed powder of cellulose powder and alkali.
(2) Glycerolation Reaction:
To 74.8 g of the obtained mixed powder of cellulose and alkali, 18 g (30% per cellulose) of ion-exchanged water was added by means of spraying, followed by mixing using a mortar. This mixture was charged in a 1-L kneader equipped with a reflux tube (PNV-1 Model, available from Irie Shokai Co., Ltd.), and warm water was flown into a jacket in a nitrogen atmosphere while stirring, thereby adjusting a jacket temperature to 50° C. Subsequently, a solution obtained by diluting 34.3 g (1.3 moles/AGU) of glycidol (available from Kanto Chemical Co., Inc.) as a glycerolating agent with 69.6 g of tetrahydrofuran (concentration of glycerolating agent: 33%) was added dropwise over 30 minutes. Thereafter, the contents were stirred at a jacket temperature of 50° C. for 3 hours. Thereafter, water at 20° C. was flown into the jacket, and the resultant was stirred for 30 minutes and then cooled, thereby obtaining 149 g of a pale yellow powder.
(3) Neutralization and Purification Step:
15.0 g of the obtained pale yellow powder was dispersed in 300 mL of a mixed solvent of ion-exchanged water/acetone/methanol=2/4/4 (volume ratio), and the alkali was neutralized with acetic acid. A solid content was filtered and collected from the dispersion liquid, and furthermore, a washing operation of dispersion using 300 mL of a mixed solvent of ion-exchanged water/acetone/methanol=2/4/4 (volume ratio) and filtration and collection was repeated twice to carry out purification, thereby 8.1 g of a glycerolated cellulose as a white solid. Subsequently, a 1% aqueous solution of the obtained glycerolated cellulose was prepared and centrifuged at 3,000 rpm (2,000×g) for 20 minutes using a centrifuge (a product name: table top type centrifuge, H-28F, available from Kokusan Co., Ltd.), thereby precipitating an insoluble matter. A supernatant of this aqueous solution was freeze-dried using a freeze dryer (FDU-1100, available from EYELA), thereby obtaining GC (1).

As a result of analysis of the obtained GC (1), the content of glycerol group was 30.3%, and MS(Gly) was 0.95. The results are shown in Table 1.

Comparative Example 4

Manufacture of Glycerolated Cellulose, GC (2)

The same operation as that in Comparative Example 3 was followed, except for changing the addition amount of the glycerolating agent to 84.4 g (3.2 mol/AGU), thereby obtaining GC (2).

As a result of analysis of the obtained GC (2), the content of glycerol group was 54.5%, and MS(Gly) was 2.62. The results are shown in Table 1.

dopropyl carbobetaine (AMPHITOL 55AB (30% aqueous solution), available from Kao Corporation), and a coconut fatty acid monoethanolamide (AMISOL CME, available from Kawaken Fine Chemicals Co., Ltd.), hair shampoos each having a composition of effective contents of respective components shown in Table 3 were prepared in the usual way. Specifically, CGC was dissolved or uniformly dispersed in water to prepare a 2% polymer solution. Separately, the respective components other than the polymer were taken in a beaker, and after heating to 80° C., the contents were stirred and uniformly dissolved. Thereafter,

TABLE 1

|  |  | Glycerolation reaction step Addition amount of glycerolating agent (mol/AGU*[1]) | Cationization reaction step Addition amount of cationizing agent (mol/AGU*[1]) | Degree of substitution of glycerol group [MS(Gly)] | Degree of substitution of cationized alkylene oxy group [MS(N+)] | Cation charge density [mmol/g] | Average polymerization degree [n] | Aqueous solution viscosity*[2] [mPa · s] |
|---|---|---|---|---|---|---|---|---|
| Example 1 | CGC (1) | 0.80 | 0.08 | 1.39 | 0.04 | 0.15 | 1332 | 26 |
| Example 2 | CGC (2) | 1.60 | 0.08 | 1.47 | 0.07 | 0.25 | 1249 | 59 |
| Example 3 | CGC (3) | 1.20 | 0.08 | 1.20 | 0.09 | 0.34 | 1249 | 34 |
| Example 4 | CGC (4) | 3.20 | 0.08 | 2.62 | 0.09 | 0.24 | 1249 | 123 |
| Example 5 | CGC (5) | 1.00 | 0.08 | 0.98 | 0.10 | 0.40 | 1249 | 40 |
| Example 6 | CGC (6) | 1.50 | 0.12 | 1.19 | 0.10 | 0.38 | 1332 | 86 |
| Example 7 | CGC (7) | 1.90 | 0.17 | 1.36 | 0.12 | 0.43 | 1249 | 23 |
| Example 8 | CGC (8) | 1.20 | 0.18 | 0.95 | 0.15 | 0.59 | 1249 | 23 |
| Example 9 | CGC (9) | 3.20 | 0.16 | 2.77 | 0.17 | 0.43 | 1249 | 103 |
| Example 10 | CGC (10) | 1.30 | 0.16 | 1.25 | 0.12 | 0.44 | 1249 | 94 |
| Example 11 | CGC (11) | 8.00 | 0.80 | 1.31 | 0.14 | 0.50 | 1233 | 221 |
| Example 12 | CGC (12) | 8.00 | 0.80 | 1.18 | 0.08 | 0.31 | 2005 | 5010 |
| Example 13 | CGC (15) | 0.80 | 0.12 | 0.86 | 0.10 | 0.42 | 1332 | 52 |
| Example 14 | CGC (16) | 3.00 | 0.20 | 2.87 | 0.17 | 0.42 | 1332 | 174 |
| Example 15 | CGC (17) | 1.25 | 0.25 | 1.56 | 0.13 | 0.44 | 1249 | 25 |
| Example 16 | CGC (18) | 8.00 | 0.40 | 1.31 | 0.07 | 0.26 | 1233 | 219 |
| Example 17 | CGC (19) | 8.00 | 1.21 | 1.04 | 0.17 | 0.64 | 2005 | 4570 |
| Comparative Example 1 | CGC (13) | 1.90 | 0.32 | 1.42 | 0.25 | 0.82 | 1249 | 27 |
| Comparative Example 2 | CGC (14) | 1.90 | 0.49 | 1.42 | 0.35 | 1.09 | 1249 | 34 |
| Comparative Example 3 | GC (1) | 1.25 | 0.00 | 0.95 |  |  | 1249 | 31 |
| Comparative Example 4 | GC (2) | 3.20 | 0.00 | 2.62 |  |  | 1249 | 61 |

*[1]Mole number relative to one mole of anhydrous glucose unit (anhydroglucose unit)
*[2]Viscosity (unit: mPa · s) of 1% by mass aqueous solution at 25° C. by B type viscometer (30 rpm)

TABLE 2

|  |  | Degree of substitution of glycerol group [MS(Gly)] | Degree of direct substitution of glycerol group [DS(Gly)] | Degree of substitution of cationized alkylene oxy group [MS(N+)] | Degree of direct substitution of cationized alkylene oxy group [DS(N+)] |
|---|---|---|---|---|---|
| Example 7 | CGC (7) | 1.36 | 0.91 | 0.12 | 0.022 |
| Example 8 | CGC (8) | 0.95 | 0.78 | 0.15 |  |
| Example 10 | CGC (10) | 1.25 | 0.83 | 0.12 | 0.120 |
| Example 11 | CGC (11) | 1.31 | 1.23 | 0.14 |  |

[Evaluation of Hair Cosmetic Composition]

Examples 18 to 29

Manufacture and Evaluation of Hair Shampoo

By using each of CGC (1) to CGC (12) and, as surfactants, a sodium polyoxyethylene alkyl sulfate (EMAL 170J (70% aqueous solution), available from Kao Corporation, average addition mole number of oxyethylene group: 1, alkyl chain length: C10 to C16), coconut fatty acid amithe polymer solution was added thereto and uniformly mixed, followed by cooling. Finally, water corresponding to the moisture evaporated off by heating was replenished.

Respective components of the following composition were taken in a beaker, heated to 80° C., and then mixed. After confirming that the components were uniformly dissolved, the solution was cooled to obtain a plain hair shampoo. A hair bunch was cleansed with the obtained plain hair shampoo and thoroughly moistened with warm water at from 35 to 40° C., and 0.5 g of each of the shampoos having a composition shown in table 3 was applied, followed by cleansing for one minute. Thereafter, the hair bunch was rinsed with warm water for 30 seconds. The thus treated hair bunch was used for a trace for evaluation, and five panelists evaluated smoothness and a long-lasting feeling of slipping at the time of rinsing the hair according to the following evaluation criteria and evaluation method. The results are shown in Table 3.

(Composition of Plain Shampoo)

| (Component) | (%) |
|---|---|
| Sodium polyoxyethylene lauryl ether sulfate (EMAL E-27C) (42.0% as EMAL E-27C (available from Kao Corporation, active component: 27%) | 11.3 |
| Coconut fatty acid N-methylethanolamide (AMINON C-11S (available from Kao Corporation)) | 3.0 |
| Citric acid | 0.2 |
| Methylparaben | 0.3 |
| Purified water | Balance |
| Total | 100.0 |

(Evaluation Criteria).
Smoothness:
5: Very good in smoothness and free from friction
4: Slightly good in smoothness and low in friction
3: Moderate
2: Poor in smoothness and grated
1: Not smoothed at all and vigorously grated
Long-Lasting Feeling:
5: Smoothness lasts very long
4: Smoothness lasts long
3: Moderate
2: Smoothness does not last
1: Smoothness does not last at all
(Evaluation Method)

The evaluation results by the five panelists were averaged to determine the grade.

Comparative Examples 5 to 9

Manufacture and Evaluation of Hair Shampoo

By using each of CGC (13) to CGC (14) and GC (1) to GC (2) and a cationized hydroxyethyl cellulose (POIZ C-80M, available from Kao Corporation), hair shampoos each having a composition shown in Table 3 were prepared and evaluated in the same manners as those in Example 18. The results are shown in Table 3.

TABLE 3

| | Hair cosmetic composition | Example | | | | | | | | |
|---|---|---|---|---|---|---|---|---|---|---|
| | (shampoo) | 18 | 19 | 20 | 21 | 22 | 23 | 24 | 25 | 26 |
| Blending composition (parts by mass) | CGC (1) | 0.3 | | | | | | | | |
| | CGC (2) | | 0.3 | | | | | | | |
| | CGC (3) | | | 0.3 | | | | | | |
| | CGC (4) | | | | 0.3 | | | | | |
| | CGC (5) | | | | | 0.3 | | | | |
| | CGC (6) | | | | | | 0.3 | | | |
| | CGC (7) | | | | | | | 0.3 | | |
| | CGC (8) | | | | | | | | 0.3 | |
| | CGC (9) | | | | | | | | | 0.3 |
| | CGC (10) | | | | | | | | | |
| | CGC (11) | | | | | | | | | |
| | CGC (12) | | | | | | | | | |
| | CGC (13) | | | | | | | | | |
| | CGC (14) | | | | | | | | | |
| | GC (1) | | | | | | | | | |
| | GC (2) | | | | | | | | | |
| | Cationized hydroxyethyl cellulose*[1] | | | | | | | | | |
| | Sodium polyoxyethylene (1) alkyl ether sulfate*[2] | 13.0 | 13.0 | 13.0 | 13.0 | 13.0 | 13.0 | 13.0 | 13.0 | 13.0 |
| | Coconut fatty acid monoethanolamide*[3] | 0.3 | 0.3 | 0.3 | 0.3 | 0.3 | 0.3 | 0.3 | 0.3 | 0.3 |
| | Coconut fatty acid amidopropyl betaine*[4] | 1.5 | 1.5 | 1.5 | 1.5 | 1.5 | 1.5 | 1.5 | 1.5 | 1.5 |
| | Sodium chloride | 0.8 | 0.8 | 0.8 | 0.8 | 0.8 | 0.8 | 0.8 | 0.8 | 0.8 |
| | pH regulator | Suitable amount | | | | | | | | |
| | Purified water | Balance | | | | | | | | |
| Evaluation | Smoothness | 3.6 | 4 | 4 | 4 | 4.6 | 5 | 4.6 | 4.6 | 4 |
| | Long-lasting feeling | 3.6 | 4.6 | 4.6 | 4.6 | 4.6 | 4.6 | 4.6 | 5 | 4.6 |

TABLE 3-continued

| | Hair cosmetic composition (shampoo) | Example 27 | Example 28 | Example 29 | Comparative Example 5 | Comparative Example 6 | Comparative Example 7 | Comparative Example 8 | Comparative Example 9 |
|---|---|---|---|---|---|---|---|---|---|
| Blending composition (parts by mass) | CGC (1) | | | | | | | | |
| | CGC (2) | | | | | | | | |
| | CGC (3) | | | | | | | | |
| | CGC (4) | | | | | | | | |
| | CGC (5) | | | | | | | | |
| | CGC (6) | | | | | | | | |
| | CGC (7) | | | | | | | | |
| | CGC (8) | | | | | | | | |
| | CGC (9) | | | | | | | | |
| | CGC (10) | 0.3 | | | | | | | |
| | CGC (11) | | 0.3 | | | | | | |
| | CGC (12) | | | 0.3 | | | | | |
| | CGC (13) | | | | 0.3 | | | | |
| | CGC (14) | | | | | 0.3 | | | |
| | GC (1) | | | | | | 0.3 | | |
| | GC (2) | | | | | | | 0.3 | |
| | Cationized hydroxyethyl cellulose[*1] | | | | | | | | 0.3 |
| | Sodium polyoxyethylene (1) alkyl ether sulfate[*2] | 13.0 | 13.0 | 13.0 | 13.0 | 13.0 | 13.0 | 13.0 | 13.0 |
| | Coconut fatty acid monoethanolamide[*3] | 0.3 | 0.3 | 0.3 | 0.3 | 0.3 | 0.3 | 0.3 | 0.3 |
| | Coconut fatty acid amidopropyl betaine[*4] | 1.5 | 1.5 | 1.5 | 1.5 | 1.5 | 1.5 | 1.5 | 1.5 |
| | Sodium chloride | 0.8 | 0.8 | 0.8 | 0.8 | 0.8 | 0.8 | 0.8 | 0.8 |
| | pH regulator | Suitable amount | | | Suitable amount | | | | |
| | Purified water | Balance | | | Balance | | | | |
| Evaluation | Smoothness | 5 | 4.6 | 5 | 3 | 3 | 2 | 2 | 3 |
| | Long-lasting feeling | 5 | 5 | 5 | 3.2 | 3.2 | 2 | 2 | 3 |

[*1]POIZ C-80M, available from Kao Corporation
[*2]Added with 18.6% of EMAL 170S (active component: 70%), available from Kao Corporation
[*3]AMISOL CME, available from Kawaken Fine Chemicals Co., Ltd.
[*4]Added with 5.0% of AMPHITOL 55AB (active component: 30%), available from Kao Corporation It is noted from Table 3 that the hair cosmetics using CGC (1) to CGC (12) according the present invention could impart excellent smoothness and its long-lasting feeling at the time of rinsing.

Examples 30 to 34

Manufacture and Evaluation of Hair Shampoo

By using CGC (6) and a surfactant and changing the content of CGC, hair shampoos each having a composition shown in Table 4 were prepared and evaluated in the same manners as those in Example 18. The results are shown in Table 4.

It is noted from Table 4 that the hair shampoos of Examples 30 to 34 could impart excellent smoothness and its long-lasting feeling at the time of rinsing.

Examples 35 to 49

Manufacture and Evaluation of Hair Shampoo

By using CGC (6) and various surfactants, hair shampoos each having a composition shown in Table 5 were prepared and evaluated in the same manners as those in Example 18. The results are shown in Table 5.

TABLE 4

| | | Examples | | | | |
|---|---|---|---|---|---|---|
| | Hair cosmetic composition (shampoo) | 30 | 31 | 32 | 33 | 34 |
| Blending composition (parts by mass) | CGC (6) | 0.01 | 0.1 | 0.5 | 1 | 3 |
| | Sodium polyoxyethylene (1) alkyl ether sulfate[*1] | 13.0 | 13.0 | 13.0 | 13.0 | 13.0 |
| | Coconut fatty acid monoethanolamide[*2] | 0.3 | 0.3 | 0.3 | 0.3 | 0.3 |
| | Coconut fatty acid amidopropyl betaine[*3] | 1.5 | 1.5 | 1.5 | 1.5 | 1.5 |
| | Sodium chloride | 0.8 | 0.8 | 0.8 | 0.8 | 0.8 |
| | pH regulator | Suitable amount | | | | |
| | Purified water | Balance | | | | |
| Evaluation | Smoothness | 4 | 4 | 5 | 5 | 5 |
| | Long-lasting feeling | 3.6 | 4 | 4 | 4 | 5 |

[*1]Added with 18.6% of EMAL 170S (active component: 70%), available from Kao Corporation
[*2]AMISOL CME, available from Kawaken Fine Chemicals Co., Ltd.
[*3]Added with 5.0% of AMPHITOL 55AB (active component: 30%), available from Kao Corporation

Comparative Example 10

Manufacture and Evaluation of Hair Shampoo

By using a cationized hydroxyethyl cellulose (POIZ C-80M, available from Kao Corporation), a hair shampoo having a composition shown in Table 5 was prepared and evaluated in the same manners as those in Example 18. The results are shown in Table 5.

TABLE 5

|  | Hair cosmetic composition | Example | | | | | | | | |
|---|---|---|---|---|---|---|---|---|---|---|
|  | (shampoo) | 35 | 36 | 37 | 38 | 39 | 40 | 41 | 42 | 43 |
| Blending composition (parts by mass) | CGC (6) | 0.3 | 0.3 | 0.3 | 0.3 | 0.3 | 0.3 | 0.3 | 0.3 | 0.3 |
|  | Cationized hydroxyethyl cellulose[17] | | | | | | | | | |
|  | Sodium alkyl sulfate[1] | 13 | | | | | | | | |
|  | Ammonium polyoxyethylene (1) alkyl ether sulfate[2] | | 13 | | | | | | | |
|  | Sodium polyoxyethylene (1) alkyl ether sulfate[3] | | | 13 | | | | | | |
|  | Sodium polyoxyethylene (2) alkyl ether sulfate[4] | | | | 13 | | | | | |
|  | Sodium polyoxyethylene (4.5) alkyl ether acetate[5] | | | | | 13 | | | | |
|  | Sodium polyoxyethylene (2) alkyl ether sulfosuccinate[6] | | | | | | 13 | | | |
|  | Sodium acyl glutamate[7] | | | | | | | 13 | | |
|  | Coconut fatty acid monoethanolamide[8] | | | | | | | | | |
|  | Coconut fatty acid methyl ethanolamide[9] | | | | | | | | | |
|  | Lauryl carboxymethylhydroxy imidazolium betaine[10] | | | | | | | | 13 | |
|  | Lauryl hydroxy sulfobetaine[11] | | | | | | | | | |
|  | Coconut fatty acid amide propylbetaine[12] | | | | | | | | | |
|  | Polyoxyethylene (3) lauryl ether[13] | | | | | | | | | |
|  | Polyoxyethylene (12) lauryl ether[14] | | | | | | | | | |
|  | Alkyl glucoside[15] | | | | | | | | | 13 |
|  | Cetyltrimethylammonium chloride[16] | | | | | | | | | |
|  | pH regulator | Suitable amount | | | | | | | | |
|  | Purified water | Balance | | | | | | | | |
| Evaluation | Smoothness | 3.6 | 3.6 | 3.6 | 4 | 4 | 4 | 3.6 | 4 | 3.6 |
|  | Long-lasting feeling | 3.6 | 3.6 | 3.6 | 4 | 4 | 4 | 3 | 3.6 | 3.6 |

|  | Hair cosmetic composition | Example | | | | | | Comparative Example |
|---|---|---|---|---|---|---|---|---|
|  | (shampoo) | 44 | 45 | 46 | 47 | 48 | 49 | 10 |
| Blending composition (parts by mass) | CGC (6) | 0.3 | 0.3 | 0.3 | 0.3 | 0.3 | 0.3 | |
|  | Cationized hydroxyethyl cellulose[17] | | | | | | | 0.3 |
|  | Sodium alkyl sulfate[1] | | | | | | | |
|  | Ammonium polyoxyethylene (1) alkyl ether sulfate[2] | | | | | | | |
|  | Sodium polyoxyethylene (1) alkyl ether sulfate[3] | | | | | | 13 | 13 |

TABLE 5-continued

|  |  |  |  |  |  |  |  |
|---|---|---|---|---|---|---|---|
| Sodium polyoxyethylene (2) alkyl ether sulfate*⁴ | 13 | 13 | 13 | 13 | 13 |  |  |
| Sodium polyoxyethylene (4.5) alkyl ether acetate*⁵ |  |  |  |  |  |  |  |
| Sodium polyoxyethylene (2) alkyl ether sulfosuccinate*⁶ |  |  |  |  |  |  |  |
| Sodium acyl glutamate*⁷ |  |  |  |  |  |  |  |
| Coconut fatty acid monoethanolamide*⁸ | 2 |  |  |  |  |  | 0.3 |
| Coconut fatty acid methyl ethanolamide*⁹ |  | 2 |  |  |  |  |  |
| Lauryl carboxymethylhydroxy imidazolium betaine*¹⁰ |  |  |  |  |  |  |  |
| Lauryl hydroxy sulfobetaine*¹¹ |  |  | 2 |  |  |  |  |
| Coconut fatty acid amide propylbetaine*¹² |  |  |  |  |  |  | 1.5 |
| Polyoxyethylene (3) lauryl ether*¹³ |  |  |  | 2 |  |  |  |
| Polyoxyethylene (12) lauryl ether*¹⁴ |  |  |  |  | 2 |  |  |
| Alkyl glucoside*¹⁵ |  |  |  |  |  |  |  |
| Cetyltrimethylammonium chloride*¹⁶ |  |  |  |  |  | 1 |  |
| pH regulator |  |  | Suitable amount |  |  |  | Suitable amount |
| Purified water |  |  | Balance |  |  |  | Balance |
| Evaluation — Smoothness | 4 | 4 | 3.6 | 3.6 | 3.6 | 4 | 3 |
| Evaluation — Long-lasting feeling | 3.6 | 4 | 3.6 | 3.6 | 3.6 | 3.6 | 3 |

*¹Added with 13.1% of EMAL 0 (active component: 99%), available from Kao Corporation
*²Added with 18.6% of EMAL 170S-A (active component: 70%), available from Kao Corporation
*³Added with 18.6% of EMAL 170J (active component: 70%), available from Kao Corporation
*⁴Added with 18.6% of EMAL 270S (active component: 70%), available from Kao Corporation
*⁵Added with 14.1% of KAO AKYPO RLM-45 (active component: 92%), available from Kao Corporation
*⁶Added with 35.1% of LIPOLAN LB-440 (active component: 37%), available from Lion Corporation
*⁷AMISOFT LS-11, available from Ajinomoto Co., Inc.
*⁸AMISOL CME, available from Kawaken Fine Chemicals Co., Ltd.
*⁹AMINON C-11S, available from Kao Corporation
*¹⁰AMPHITOL 20-YB, available from Kao Corporation
*¹¹Added with 6.7% of AMPHITOL 20HD (active component: 30%), available from Kao Corporation
*¹²Added with 5.0% of AMPHITOL 55AB (active component: 30%), available from Kao Corporation
*¹³EMALGEN 103, available from Kao Corporation
*¹⁴EMALGEN 120, available from Kao Corporation
*¹⁵Added with 32.5% of MIDOL 10 (active component: 40%), available from Kao Corporation
*¹⁶Added with 3.3% of QUARTAMIN 60W (active component: 30%), available from Kao Corporation
*¹⁷POIZ C-80M, available from Kao Corporation It is noted from Table 5 that the hair shampoos of Examples 35 to 49 could impart excellent smoothness and its long-lasting feeling at the time of rinsing.

Examples 50 to 103

Manufacture and Evaluation of Shampoo

By using each of CGC (1), CGC (4), CGC (6), CGC (8), CGC (12), and CGC (15) to CGC (19), shampoos each having a composition shown in Tables 6 to 10 were prepared in the usual way.

Specifically, CGC was dissolved or uniformly dispersed in water, suitable amounts of water and a surfactant were taken in a beaker, and the contents were uniformly mixed by heating at 60° C., followed by cooling to 50° C. An oil was then added thereto, and after uniformly mixing, the mixture was emulsified with stirring for 30 minutes and then cooled. Finally, water corresponding to the moisture evaporated off by heating was replenished, and the pH was measured. The pH was adjusted to 5 with a pH regulator (50% citric acid aqueous solution).

As for Examples 64 to 80, CGC was dissolved or uniformly dispersed in water, suitable amounts of water and a surfactant were taken in a beaker, and the contents were uniformly mixed by heating at 60° C. An oil was then added thereto, and the contents were uniformly mixed and then cooled. Finally, water corresponding to the moisture evaporated off by heating was replenished, and the pH was measured. The pH was adjusted to with a pH regulator (50% citric acid aqueous solution).

A hair bunch was cleansed with the above-described plain hair shampoo and thoroughly moistened with warm water at from 35 to 40° C., and 0.5 g of each of the shampoos of Examples 50 to 103 was applied, followed by cleansing for one minute. Thereafter, the hair bunch was rinsed with warm water for 30 seconds, the moisture was removed using a towel, and the hair bunch was neatly combed and then dried with warm air of a dryer. Lastly, the hair bunch was neatly combed, thereby obtaining a trace for evaluation.

Five panelists evaluated smoothness and a long-lasting feeling of smoothness at the time of rinsing the hair and a moist feeling and softness after drying according to the following evaluation criteria and evaluation method. The results are shown in Tables 6 to 10.

Comparative Example 15 is defined as a standard score of 3, and when the average grade by the five panelists is a score of 3.4 or more, it may be said that the sample explicitly has an excellent performance in the evaluation.

(Evaluation Criteria and Evaluation Method)

Smoothness at the Time of Rinsing:
5: Very good in slipping
4: Good in slipping
3: Moderate in slipping (on the basis of the smoothness of Comparative Example 15)
2: Poor in slipping
1: Very poor in slipping Long-Lasting Feeling of Smoothness:
5: Smoothness lasts very long
4: Smoothness lasts long
3: Moderate (on the basis of the long-lasting feeling of Comparative Example 15)
2: Smoothness does not last
1: Smoothness does not last at all Moist Feeling after Drying:
5: Very strong in moist feeling
4: Strong in moist feeling
3: Moderate (on the basis of the moist feeling of Comparative Example 15)
2: Weak in moist feeling
1: Very weak in moist feeling Softness after Drying:
5: Very soft
4: Soft
3: Moderate (on the basis of the softness of Comparative Example 15)
2: Hard
1: Very hard Comparative Examples 11 to 17

Shampoos using various polymers shown in Table 6 in place of CGC of Example 50 (Comparative Examples 11 to 15 and 17) and a shampoo in which CGC of Example 50 was not added (Comparative Example 16) were prepared in the same manner as that in Example 50. Incidentally, the pH of the shampoos of Comparative Examples 11 to 17 was adjusted to 5.

The results of evaluation of Shampoos of Comparative Examples 11 to 17 are shown in Tables 6 and 10.

TABLE 6

| Hair cosmetic composition (shampoo) | | | Example | | | | | | | | | |
|---|---|---|---|---|---|---|---|---|---|---|---|---|
| | | | 50 | 51 | 52 | 53 | 54 | 55 | 56 | 57 | 58 | 59 |
| Blending composition (parts by mass) | CGC of the present invention | CGC (1) | 0.3 | | | | | | | | | |
| | | CGC (15) | | 0.3 | | | | | | | | |
| | | CGC (6) | | | 0.3 | | | | | | | |
| | | CGC (8) | | | | 0.3 | | | | | | |
| | | CGC (16) | | | | | 0.3 | | | | | |
| | | CGC (4) | | | | | | 0.3 | | | | |
| | | CGC (17) | | | | | | | 0.3 | | | |
| | | CGC (18) | | | | | | | | 0.3 | | |
| | | CGC (19) | | | | | | | | | 0.3 | |
| | | CGC (12) | | | | | | | | | | 0.3 |
| | Other polymer | CGC (13) | | | | | | | | | | |
| | | CGC (14) | | | | | | | | | | |
| | | GC (1) | | | | | | | | | | |
| | | GC (2) | | | | | | | | | | |
| | | Cationized hydroxyethyl cellulose[*1] | | | | | | | | | | |
| | Surfactant | Sodium laureth-1 sulfate[*2] | 13.0 | 13.0 | 13.0 | 13.0 | 13.0 | 13.0 | 13.0 | 13.0 | 13.0 | 13.0 |
| | | Coconut fatty acid amidopropyl betaine[*3] | 1.5 | 1.5 | 1.5 | 1.5 | 1.5 | 1.5 | 1.5 | 1.5 | 1.5 | 1.5 |
| | | Coconut fatty acid monoethanolamide[*4] | 0.3 | 0.3 | 0.3 | 0.3 | 0.3 | 0.3 | 0.3 | 0.3 | 0.3 | 0.3 |
| | Oil | Highly polymerized dimethyl polysiloxane[*5] | 1.0 | 1.0 | 1.0 | 1.0 | 1.0 | 1.0 | 1.0 | 1.0 | 1.0 | 1.0 |
| | | pH regulator | Suitable amount | | | | | | | | | |
| | | Purified water | Balance | | | | | | | | | |
| Mass ratio [CGC/surfactant] | | | 0.02 | 0.02 | 0.02 | 0.02 | 0.02 | 0.02 | 0.02 | 0.02 | 0.02 | 0.02 |
| Mass ratio [CGC/oil] | | | 0.3 | 0.3 | 0.3 | 0.3 | 0.3 | 0.3 | 0.3 | 0.3 | 0.3 | 0.3 |
| Mass ratio [surfactant/oil] | | | 14.8 | 14.8 | 14.8 | 14.8 | 14.8 | 14.8 | 14.8 | 14.8 | 14.8 | 14.8 |
| Evaluation | Smoothness at the time of rinsing | | 3.4 | 4.0 | 4.0 | 3.6 | 4.2 | 3.4 | 3.4 | 4.0 | 5.0 | 5.0 |
| | Long-lasting feeling of smoothness | | 3.4 | 4.4 | 4.4 | 4.0 | 4.6 | 3.8 | 3.6 | 4.4 | 5.0 | 5.0 |
| | Moist feeling after drying | | 3.6 | 4.2 | 3.6 | 3.4 | 4.2 | 4.0 | 4.2 | 4.2 | 4.8 | 4.8 |
| | Softness after drying | | 4.0 | 3.6 | 4.0 | 3.6 | 4.0 | 3.6 | 3.6 | 4.0 | 4.6 | 4.8 |

| Hair cosmetic composition (shampoo) | | | Comparative Example | | | | | |
|---|---|---|---|---|---|---|---|---|
| | | | 11 | 12 | 13 | 14 | 15 | 16 |
| Blending composition (parts by mass) | CGC of the present invention | CGC (1) | | | | | | |
| | | CGC (15) | | | | | | |
| | | CGC (6) | | | | | | |
| | | CGC (8) | | | | | | |
| | | CGC (16) | | | | | | |
| | | CGC (4) | | | | | | |
| | | CGC (17) | | | | | | |
| | | CGC (18) | | | | | | |

TABLE 6-continued

|  |  |  |  |  |  |  |  |  |
|---|---|---|---|---|---|---|---|---|
|  | Other polymer | CGC (19) |  |  |  |  |  |  |
|  |  | CGC (12) |  |  |  |  |  |  |
|  |  | CGC (13) | 0.3 |  |  |  |  |  |
|  |  | CGC (14) |  | 0.3 |  |  |  |  |
|  |  | GC (1) |  |  | 0.3 |  |  |  |
|  |  | GC (2) |  |  |  | 0.3 |  |  |
|  |  | Cationized hydroxyethyl cellulose*[1] |  |  |  |  | 0.3 |  |
|  | Surfactant | Sodium laureth-1 sulfate*[2] | 13.0 | 13.0 | 13.0 | 13.0 | 13.0 | 13.0 |
|  |  | Coconut fatty acid amidopropyl betaine*[3] | 1.5 | 1.5 | 1.5 | 1.5 | 1.5 | 1.5 |
|  |  | Coconut fatty acid monoethanolamide*[4] | 0.3 | 0.3 | 0.3 | 0.3 | 0.3 | 0.3 |
|  | Oil | Highly polymerized dimethyl polysiloxane*[5] | 1.0 | 1.0 | 1.0 | 1.0 | 1.0 | 1.0 |
|  |  | pH regulator |  |  | Suitable amount |  |  |  |
|  |  | Purified water |  |  | Balance |  |  |  |
| Mass ratio [CGC/surfactant] |  |  | — | — | — | — | — | — |
| Mass ratio [CGC/oil] |  |  | — | — | — | — | — | — |
| Mass ratio [surfactant/oil] |  |  | — | — | — | — | — | — |
| Evaluation | Smoothness at the time of rinsing |  | 3.0 | 2.6 | 1.6 | 1.4 | 3.0 | 1.2 |
|  | Long-lasting feeling of smoothness |  | 3.0 | 2.6 | 1.4 | 1.4 | 3.0 | 1.0 |
|  | Moist feeling after drying |  | 2.6 | 2.6 | 2.0 | 2.0 | 3.0 | 1.6 |
|  | Softness after drying |  | 2.4 | 2.6 | 3.0 | 2.0 | 3.0 | 1.6 |

Incidentally, the details of the components used in Table 6 are shown below.

*[1]POIZ C-80M, available from Kao Corporation
*[2]EMAL 170J (active component: 70%), available from Kao Corporation
*[3]AMPHITOL 55AB (active component: 30%), available from Kao Corporation
*[4]AMISOL CME, available from Kawaken Fine Chemicals Co., Ltd.
*[5]BY22-029 (active component: 50%), available from Dow Corning Toray Co., Ltd.

TABLE 7

|  |  |  | Example |  |  |  |  |
|---|---|---|---|---|---|---|---|
| Hair cosmetic (shampoo) |  |  | 60 | 52 | 61 | 62 | 63 |
| Blending composition (parts by mass) | CGC | CGC (6) | 0.1 | 0.3 | 0.5 | 1.0 | 3 |
|  | Surfactant | Sodium laureth-1 sulfate*[1] | 13 | 13 | 13 | 13 | 13 |
|  |  | Coconut fatty acid amidopropyl betaine*[2] | 1.5 | 1.5 | 1.5 | 1.5 | 1.5 |
|  |  | Coconut fatty acid monoethanolamide*[3] | 0.3 | 0.3 | 0.3 | 0.3 | 0.3 |
|  | Oil | Highly polymerized dimethyl polysiloxane*[4] | 1.0 | 1.0 | 1.0 | 1.0 | 1.0 |
|  |  | pH regulator | Suitable amount |  |  |  |  |
|  |  | Purified water | Balance |  |  |  |  |
| Mass ratio [CGC/surfactant] |  |  | 0.0068 | 0.0203 | 0.0338 | 0.0676 | 0.2027 |
| Mass ratio [CGC/oil] |  |  | 0.1 | 0.3 | 0.5 | 1.0 | 3.0 |
| Mass ratio [surfactant/oil] |  |  | 14.8 | 14.8 | 14.8 | 14.8 | 14.8 |
| Evaluation | Smoothness at the time of rinsing |  | 3.4 | 4.0 | 4.4 | 4.8 | 5.0 |
|  | Long-lasting feeling of smoothness |  | 3.4 | 4.4 | 4.4 | 4.8 | 5.0 |
|  | Moist feeling after drying |  | 3.4 | 3.6 | 4.0 | 4.0 | 4.0 |
|  | Softness after drying |  | 3.6 | 4.0 | 4.0 | 3.8 | 3.6 |

*[1]EMAL 170J (active component: 70%), available from Kao Corporation
*[2]AMPHITOL 55AB (active component: 30%), available from Kao Corporation
*[3]AMISOL CME, available from Kawaken Fine Chemicals Co., Ltd.
*[4]Trade name: BY22-029 (active component: 50%), available from Dow Corning Toray Co., Ltd.

TABLE 8

| | | | Example | | | | | | | | | | | |
|---|---|---|---|---|---|---|---|---|---|---|---|---|---|---|
| | | Hair cosmetic (shampoo) | 64 | 65 | 66 | 67 | 68 | 69 | 70 | 71 | 72 | 73 | 74 | 75 |
| Blending composition (parts by mass) | CGC | CGC (6) | 0.3 | 0.3 | 0.3 | 0.3 | 0.3 | 0.3 | 0.3 | 0.3 | 0.3 | 0.3 | 0.3 | 0.3 |
| | Surfactant | Sodium laureth-1 sulfate[1] | 13 | 13 | 13 | 13 | 13 | 13 | 13 | 13 | 13 | 13 | 13 | 13 |
| | | Coconut fatty acid amidopropyl betaine[2] | 1.5 | 1.5 | 1.5 | 1.5 | 1.5 | 1.5 | 1.5 | 1.5 | 1.5 | 1.5 | 1.5 | 1.5 |
| | | Coconut fatty acid monoethanolamide[3] | 0.3 | 0.3 | 0.3 | 0.3 | 0.3 | 0.3 | 0.3 | 0.3 | 0.3 | 0.3 | 0.3 | 0.3 |
| | Oil | Oleic acid[4] | 1 | | | | | | | | | | | |
| | | Isostearic acid[5] | | 1 | | | | | | | | | | |
| | | Macadamia nut oil[6] | | | 1 | | | | | | | | | |
| | | Avocado oil[7] | | | | 1 | | | | | | | | |
| | | Sunflower oil[8] | | | | | 1 | | | | | | | |
| | | Dipentaerythrityl (hydroxystearate/stearate/rosinate)[9] | | | | | | 1 | | | | | | |
| | | Myristyl myristate[10] | | | | | | | 1 | | | | | |
| | | Isopropyl palmitate[11] | | | | | | | | 1 | | | | |
| | | Cetyl palmitate[12] | | | | | | | | | 1 | | | |
| | | Stearyl stearate[13] | | | | | | | | | | 1 | | |
| | | Squalane[14] | | | | | | | | | | | 1 | |
| | | Liquid paraffin[15] | | | | | | | | | | | | 1 |
| | | Paraffin wax[16] | | | | | | | | | | | | |
| | | Behenyl alcohol[17] | | | | | | | | | | | | |
| | | Dioctyl ether[18] | | | | | | | | | | | | |
| | | Dioctyl carbonate[19] | | | | | | | | | | | | |
| | | PPG-3 benzyl ether myristate[20] | | | | | | | | | | | | |
| | | Dimethiconol[21] | | | | | | | | | | | | |
| | | Polyether-modified silicone[22] | | | | | | | | | | | | |
| | | Polyether-modified silicone[23] | | | | | | | | | | | | |
| | | Highly polymerized dimethyl siloxane[24] | | | | | | | | | | | | |
| | | Highly polymerized dimethyl siloxane[25] | | | | | | | | | | | | |
| | | Amino-modified highly polymerized dimethyl polysiloxane[26] | | | | | | | | | | | | |
| | | pH regulator | Suitable amount | | | | | | | | | | | |
| | | Purified water | Balance | | | | | | | | | | | |
| Evaluation | | Smoothness at the time of rinsing | 4.0 | 3.6 | 3.4 | 3.6 | 3.6 | 3.4 | 4.0 | 3.8 | 3.6 | 4.0 | 4.0 | 4.0 |
| | | Long-lasting feeling of smoothness | 4.0 | 3.6 | 4.0 | 3.8 | 3.4 | 3.4 | 4.0 | 3.8 | 3.6 | 4.0 | 4.0 | 4.0 |
| | | Moist feeling after drying | 3.8 | 4.0 | 4.4 | 3.2 | 4.4 | 4.4 | 3.8 | 3.6 | 3.2 | 3.4 | 4.4 | 3.4 |
| | | Softness after drying | 4.0 | 4.0 | 4.4 | 3.8 | 4.0 | 4.6 | 4.6 | 4.2 | 3.4 | 4.0 | 4.0 | 3.4 |

| | | | Example | | | | | | | | | | |
|---|---|---|---|---|---|---|---|---|---|---|---|---|---|
| | | Hair cosmetic (shampoo) | 76 | 77 | 78 | 79 | 80 | 81 | 82 | 83 | 84 | 85 | 86 |
| Blending composition (parts by mass) | CGC | CGC (6) | 0.3 | 0.3 | 0.3 | 0.3 | 0.3 | 0.3 | 0.3 | 0.3 | 0.3 | 0.3 | 0.3 |
| | Surfactant | Sodium laureth-1 sulfate[1] | 13 | 13 | 13 | 13 | 13 | 13 | 13 | 13 | 13 | 13 | 13 |
| | | Coconut fatty acid amidopropyl betaine[2] | 1.5 | 1.5 | 1.5 | 1.5 | 1.5 | 1.5 | 1.5 | 1.5 | 1.5 | 1.5 | 1.5 |
| | | Coconut fatty acid monoethanolamide[3] | 0.3 | 0.3 | 0.3 | 0.3 | 0.3 | 0.3 | 0.3 | 0.3 | 0.3 | 0.3 | 0.3 |
| | Oil | Oleic acid[4] | | | | | | | | | | | |
| | | Isostearic acid[5] | | | | | | | | | | | |
| | | Macadamia nut oil[6] | | | | | | | | | | | |
| | | Avocado oil[7] | | | | | | | | | | | |
| | | Sunflower oil[8] | | | | | | | | | | | |
| | | Dipentaerythrityl (hydroxystearate/stearate/rosinate)[9] | | | | | | | | | | | |
| | | Myristyl myristate[10] | | | | | | | | | | | |
| | | Isopropyl palmitate[11] | | | | | | | | | | | |
| | | Cetyl palmitate[12] | | | | | | | | | | | |
| | | Stearyl stearate[13] | | | | | | | | | | | |
| | | Squalane[14] | | | | | | | | | | | |
| | | Liquid paraffin[15] | | | | | | | | | | | |
| | | Paraffin wax[16] | 1 | | | | | | | | | | |
| | | Behenyl alcohol[17] | | 1 | | | | | | | | | |
| | | Dioctyl ether[18] | | | 1 | | | | | | | | |
| | | Dioctyl carbonate[19] | | | | 1 | | | | | | | |
| | | PPG-3 benzyl ether myristate[20] | | | | | 1 | | | | | | |
| | | Dimethiconol[21] | | | | | | 1 | | | | | |
| | | Polyether-modified silicone[22] | | | | | | | 1 | | | | |

TABLE 8-continued

|  |  |  |  |  |  |  |  |  |  |  |  |
|---|---|---|---|---|---|---|---|---|---|---|---|
|  | Polyether-modified silicone*23 |  |  |  |  |  |  | 1 |  |  |  |
|  | Highly polymerized dimethyl siloxane*24 |  |  |  |  |  |  |  | 1 |  |  |
|  | Highly polymerized dimethyl siloxane*25 |  |  |  |  |  |  |  |  | 1 |  |
|  | Amino-modified highly polymerized dimethyl polysiloxane*26 |  |  |  |  |  |  |  |  |  | 1 |
|  | pH regulator | Suitable amount |  |  |  |  |  |  |  |  |  |
|  | Purified water | Balance |  |  |  |  |  |  |  |  |  |
| Evaluation | Smoothness at the time of rinsing | 4.0 | 4.0 | 3.4 | 3.4 | 3.0 | 4.0 | 3.6 | 3.4 | 4.0 | 4.0 | 4.0 |
|  | Long-lasting feeling of smoothness | 4.0 | 4.0 | 3.4 | 3.4 | 3.0 | 4.0 | 3.4 | 3.4 | 4.0 | 4.0 | 4.2 |
|  | Moist feeling after drying | 4.6 | 3.4 | 3.4 | 3.8 | 4.0 | 3.4 | 3.6 | 3.6 | 4.0 | 4.6 | 3.4 |
|  | Softness after drying | 4.6 | 3.4 | 3.4 | 3.6 | 3.4 | 3.6 | 3.6 | 3.6 | 4.0 | 4.0 | 4.4 |

Incidentally, the details of the components used in Table 8 are shown below.
*[1] EMAL 170J (active component: 70%), available from Kao Corporation
*[2] AMPHITOL 55AB (active component: 30%), available from Kao Corporation
*[3] AMISOL CME, available from Kawaken Fine Chemicals Co., Ltd.
*[4] LUNAC LO-V, available from Kao Corporation
*[5] ISOSTEARIC ACID EX, available from Kokyu Alcohol Kogyo Co., Ltd.
*[6] MACADAMIA NUT OIL, available from Nikko Chemicals Co., Ltd.
*[7] PURIFIED AVOCADO OIL, available from Nikko Chemicals Co., Ltd.
*[8] Edible sunflower oil, available from Nihon Ryutsu Sangyo Co., Ltd.
*[9] COSMOL 168ARV, available from The Nisshin OilliO Group, Ltd.
*[10] EXEPARL MYM, available from Kao Corporation
*[11] EXEPARL IPP, available from Kao Corporation
*[12] CUTINA CP, available from Cognis
*[13] EXEPARL SS, available from Kao Corporation
*[14] SQUALANE, available from Nikko Chemicals Co., Ltd.
*[15] HI-CALL K-230, available from Kaneda Co., Ltd.
*[16] PARAFFIN WAX125, available from Nippon Seiro Co., Ltd.
*[17] KALCOL 220-80, available from Kao Corporation
*[18] CETIOL OE, available from Cognis
*[19] CETIOL CC, available from Cognis
*[20] CRODAMOL STS, available from Croda
*[21] 1785 EMULSION (active component: 60%), available from Dow Corning Toray Co., Ltd.
*[22] SOFCARE GS-G, available from Kao Corporation
*[23] KF6011, available from Shin-Etsu Chemical Co., Ltd.
*[24] BY22-050A (active component: 50%), available from Dow Corning Toray Co., Ltd.
*[25] BY22-029 (active component: 51%), available from Dow Corning Toray Co., Ltd.
*[26] SM8904 (active component: 40%), available from Dow Corning Toray Co., Ltd.

TABLE 9

|  |  |  | Example |  |  |  |  |
|---|---|---|---|---|---|---|---|
|  |  | Hair cosmetic (shampoo) | 87 | 88 | 52 | 89 | 90 |
| Blending composition (parts by mass) | CGC | CGC (6) | 0.3 | 0.3 | 0.3 | 0.3 | 0.3 |
|  | Surfactant | Sodium laureth-1 sulfate*[1] | 13 | 13 | 13 | 13 | 13 |
|  |  | Coconut fatty acid amidopropyl betaine*[2] | 1.5 | 1.5 | 1.5 | 1.5 | 1.5 |
|  |  | Coconut fatty acid monoethanolamide*[3] | 0.3 | 0.3 | 0.3 | 0.3 | 0.3 |
|  | Oil | Highly polymerized dimethyl polysiloxane*[4] | 0.01 | 0.1 | 1.0 | 5.0 | 10 |
|  |  | pH regulator | Suitable amount |  |  |  |  |
|  |  | Purified water | Balance |  |  |  |  |
| Mass ratio [CGC/surfactant] |  |  | 0.02 | 0.02 | 0.02 | 0.02 | 0.02 |
| Mass ratio [CGC/oil] |  |  | 30 | 3.0 | 0.3 | 0.06 | 0.03 |
| Mass ratio [surfactant/oil] |  |  | 1480 | 148 | 14.8 | 2.96 | 1.48 |
| Evaluation | Smoothness at the time of rinsing |  | 4.0 | 4.0 | 4.0 | 3.6 | 3.6 |
|  | Long-lasting feeling of smoothness |  | 4.0 | 4.0 | 4.4 | 3.6 | 3.6 |
|  | Moist feeling after drying |  | 3.4 | 3.4 | 3.6 | 4.8 | 5.0 |
|  | Softness after drying |  | 3.8 | 3.8 | 4.0 | 3.6 | 3.2 |

*[1] EMAL 170J (active component: 70%), available from Kao Corporation
*[2] AMPHITOL 55AB (active component: 30%), available from Kao Corporation
*[3] AMISOL CME, available from Kawaken Fine Chemicals Co., Ltd.
*[4] BY22-029 (active component: 50%), available from Dow Corning Toray Co., Ltd.

TABLE 10

| | | | Example | | | | | | | |
|---|---|---|---|---|---|---|---|---|---|---|
| | | Hair cosmetic (shampoo) | 91 | 92 | 93 | 94 | 95 | 96 | 97 | 98 |
| Blending composition (parts by mass) | CGC | CGC (6) | 0.3 | 0.3 | 0.3 | 0.3 | 0.3 | 0.3 | 0.3 | 0.3 |
| | Others Surfactant | Cationized hydroxyethyl cellulose*1 | | | | | | | | |
| | | Sodium lauryl sulfate*2 | 13.0 | | | | | | | |
| | | Ammonium laureth-1 sulfate*3 | | 13.0 | | | | | | |
| | | Sodium laureth-2 sulfate*4 | | | 13.0 | | | | | |
| | | Sodium laureth-4,5 acetate*5 | | | | 13.0 | | | | |
| | | Sodium laureth-2 sulfosuccinate*6 | | | | | 13.0 | | | |
| | | Sodium acyl glutamate*7 | | | | | | 13.0 | | |
| | | Coconut fatty acid monoethanolamide*8 | | | | | | | | |
| | | Coconut fatty acid methyl ethanolamide*9 | | | | | | | | |
| | | Lauryl carboxymethylhydroxy imidazolium betaine*10 | | | | | | | 13.0 | |
| | | Lauryl hydroxy sulfobetaine*11 | | | | | | | | |
| | | Laureth-3*12 | | | | | | | | |
| | | Laureth-12*13 | | | | | | | | |
| | | Alkyl glucoside*14 | | | | | | | | 13.0 |
| | Oil | Highly polymerized dimethyl polysiloxane*15 | 1.0 | 1.0 | 1.0 | 1.0 | 1.0 | 1.0 | 1.0 | 1.0 |
| | | pH regulator | | | | Suitable amount | | | | |
| | | Purified water | | | | Balance | | | | |
| Evaluation | | Smoothness at the time of rinsing | 3.4 | 3.8 | 4.0 | 4.6 | 4.2 | 3.6 | 4.2 | 4.0 |
| | | Long-lasting feeling of smoothness | 3.4 | 3.8 | 3.8 | 4.2 | 4.6 | 3.6 | 4.2 | 4.0 |
| | | Moist feeling after drying | 3.4 | 3.6 | 3.8 | 4.2 | 5.0 | 4.0 | 3.8 | 4.2 |
| | | Softness after drying | 3.4 | 3.6 | 3.6 | 3.4 | 3.4 | 3.8 | 4.4 | 3.6 |

| | | | Example | | | | | Comparative Example |
|---|---|---|---|---|---|---|---|---|
| | | Hair cosmetic (shampoo) | 99 | 100 | 101 | 102 | 103 | 17 |
| Blending composition (parts by mass) | CGC | CGC (6) | 0.3 | 0.3 | 0.3 | 0.3 | 0.3 | |
| | Others Surfactant | Cationized hydroxyethyl cellulose*1 | | | | | | 0.3 |
| | | Sodium lauryl sulfate*2 | | | | | | |
| | | Ammonium laureth-1 sulfate*3 | | | | | | 13 |
| | | Sodium laureth-2 sulfate*4 | 13.0 | 13.0 | 13.0 | 13.0 | 13.0 | |
| | | Sodium laureth-4,5 acetate*5 | | | | | | |
| | | Sodium laureth-2 sulfosuccinate*6 | | | | | | |
| | | Sodium acyl glutamate*7 | | | | | | |
| | | Coconut fatty acid monoethanolamide*8 | 2.0 | | | | | |
| | | Coconut fatty acid methyl ethanolamide*9 | | 2.0 | | | | |
| | | Lauryl carboxymethylhydroxy imidazolium betaine*10 | | | | | | |
| | | Lauryl hydroxy sulfobetaine*11 | | | 2.0 | | | |
| | | Laureth-3*12 | | | | 2.0 | | |
| | | Laureth-12*13 | | | | | 2.0 | |
| | | Alkyl glucoside*14 | | | | | | |
| | Oil | Highly polymerized dimethyl polysiloxane*15 | 1.0 | 1.0 | 1.0 | 1.0 | 1.0 | 1.0 |
| | | pH regulator | | | Suitable amount | | | |
| | | Purified water | | | Balance | | | |
| Evaluation | | Smoothness at the time of rinsing | 3.8 | 3.8 | 4.2 | 3.6 | 3.6 | 3.0 |
| | | Long-lasting feeling of smoothness | 3.8 | 3.8 | 4.2 | 3.6 | 3.6 | 3.0 |
| | | Moist feeling after drying | 3.8 | 4.0 | 4.2 | 4.0 | 4.0 | 3.0 |
| | | Softness after drying | 3.6 | 3.8 | 3.8 | 3.8 | 3.8 | 3.0 |

Incidentally, the details of the components used in Table 10 are shown below.
*1POIZ C-80M, available from Kao Corporation
*2EMAL 0, available from Kao Corporation
*3EMAL 170S-A (active component: 70%), available from Kao Corporation
*4EMAL 270S (active component: 70%), available from Kao Corporation
*5KAO AKYPO RMN45NV (active component: 23.5%), available from Kao Corporation
*6RIKAMILD ES-100 (active component: 30%), available from New Japan Chemical Co., Ltd.
*7AMISOFT CS-11, available from Ajinomoto Co., Inc.
*8AMISOL CME, available from Kawaken Fine Chemicals Co., Ltd.
*9AMINON C-11S, available from Kao Corporation
*10AMPHITOL 20YB (active component: 30%), available from Kao Corporation
*11AMPHITOL 20HD (active component: 30%), available from Kao Corporation
*12EMALGEN 103, available from Kao Corporation
*13EMALGEN 120, available from Kao Corporation
*14MIDOL 10 (active component: 40%), available from Kao Corporation
*15BY22-029 (active component: 50%), available from Dow Corning Toray Co., Ltd.

It is noted from Tables 6 to 10 that the shampoos of Examples 50 to 103 are an excellent shampoo capable of imparting smoothness and long-lasting feeling of smoothness at the time of rinsing and moist feeling and softness after drying.

Examples 104 to 117

Manufacture and Evaluation of Conditioner

By using CGC (6) obtained in Example 6, conditioners were prepared in the usual way so as to have each of compositions of Examples 104 to 117 shown in Tables 11 to 13. Specifically, CGC, a suitable amount of water, and a suitable amount of a pH regulator were taken in a beaker and heated for dissolution at 80° C. A mixture of a surfactant, cetyl alcohol, and stearyl alcohol dissolved at 80° C. was added thereto, and the contents were emulsified and stirred for one hour. The resultant was cooled to 50° C., to which was then added an oil, and the contents were uniformly mixed. Finally, water corresponding to the moisture evaporated off by heating was replenished, and the pH was measured. The pH was adjusted to 5 with a pH regulator (a 50% citric acid aqueous solution and a 48% sodium hydroxide aqueous solution) as the need arose.

A hair bunch was cleansed with the plain hair shampoo used in Example 50 and thoroughly moistened with warm water at from 35 to 40° C., and 1 g of each of the conditioners of Examples 104 to 117 was applied for one minute. The hair bunch was rinsed with warm water for 30 seconds, the moisture was removed using a towel, and the hair bunch was neatly combed. Thereafter, the hair bunch was dried with warm air of a dryer. Lastly, the hair bunch was neatly combed, thereby obtaining a trace for evaluation. Five panelists evaluated smoothness and long-lasting feeling of smoothness at the time of rinsing the hair and a moist feeling and softness after drying according to the same evaluation method as that in Examples 50 to 103. The results are shown in Tables 11 to 13.

Comparative Example 18 is defined as a standard score of 3, and when the average grade by the five panelists is a score of 3.4 or more, it may be said that the sample explicitly has an excellent performance in the evaluation.

Comparative Examples 18 and 19

A conditioner using a cationized hydroxyethyl cellulose in place of CGC (6) obtained in Example 6 (Comparative Example 18) and a conditioner in which CGC (6) was not used (Comparative Example 19) were prepared and evaluated in the same manners as those in Example 104. Incidentally, the pH of the conditioners of Comparative Examples 18 and 19 was adjusted to 5. The results are shown in Table 11.

TABLE 11

| | | | Example | | | | | | Comparative Example | |
|---|---|---|---|---|---|---|---|---|---|---|
| | Hair cosmetic (conditioner) | | 104 | 105 | 106 | 107 | 108 | 109 | 18 | 19 |
| Blending composition (parts by mass) | CGC | CGC (6) | 0.05 | 0.10 | 0.30 | 0.50 | 1.00 | 3.00 | | |
| | Others | Cationized hydroxyethyl cellulose*1 | | | | | | | 0.3 | |
| | Surfactant | Behenyltrimethylammonium chloride*2 | 1.5 | 1.5 | 1.5 | 1.5 | 1.5 | 1.5 | 1.5 | 1.5 |
| | Oil | Cetyl alcohol*3 | 1.3 | 1.3 | 1.3 | 1.3 | 1.3 | 1.3 | 1.3 | 1.3 |
| | | Stearyl alcohol*4 | 2.6 | 2.6 | 2.6 | 2.6 | 2.6 | 2.6 | 2.6 | 2.6 |
| | | Highly polymerized dimethyl polysiloxane*5 | 1.0 | 1.0 | 1.0 | 1.0 | 1.0 | 1.0 | 1.0 | 1.0 |
| | | pH regulator | | | | Suitable amount | | | | |
| | | Purified water | | | | Balance | | | | |
| Mass ratio [CGC/surfactant] | | | 0.0333 | 0.0667 | 0.20 | 0.3333 | 0.6667 | 2.00 | — | — |
| Mass ratio [CGC/oil] | | | 0.01 | 0.02 | 0.06 | 0.10 | 0.20 | 0.61 | — | — |
| Mass ratio [surfactant/oil] | | | 0.31 | 0.31 | 0.31 | 0.31 | 0.31 | 0.31 | — | — |
| Evaluation | Smoothness at the time of rinsing | | 3.4 | 3.6 | 3.6 | 4.0 | 4.0 | 3.4 | 3.0 | 2.6 |
| | Long-lasting feeling of smoothness | | 3.4 | 3.6 | 4.0 | 4.0 | 3.6 | 3.4 | 3.0 | 3.0 |
| | Moist feeling after drying | | 3.4 | 3.4 | 3.6 | 3.6 | 3.6 | 4.0 | 3.0 | 3.0 |
| | Softness after drying | | 4.0 | 4.0 | 4.0 | 4.0 | 3.8 | 4.0 | 3.0 | 3.4 |

*1POIZ C-80M, available from Kao Corporation
*2QUARTAMIN 2285E-E (active component: 58%), available from Kao Corporation
*3KALCOL 6098, available from Kao Corporation
*4KALCOL 8098, available from Kao Corporation
*5BY22-029 (active component: 50%), available from Dow Corning Toray Co., Ltd.

TABLE 12

| | | | Example | | | | |
|---|---|---|---|---|---|---|---|
| | Hair cosmetic (conditioner) | | 110 | 111 | 106 | 112 | 113 |
| Blending composition (parts by mass) | CGC | CGC (6) | 0.30 | 0.30 | 0.30 | 0.30 | 0.30 |
| | Surfactant | Behenyltrimethylammonium chloride*1 | 1.5 | 1.5 | 1.5 | 1.5 | 1.5 |
| | Oil | Cetyl alcohol*2 | 1.3 | 1.3 | 1.3 | 1.3 | 1.3 |
| | | Stearyl alcohol*3 | 2.6 | 2.6 | 2.6 | 2.6 | 2.6 |
| | | Highly polymerized dimethyl polysiloxane*4 | 0.1 | 0.5 | 1.0 | 5.0 | 10 |
| | | pH regulator | | | Suitable amount | | |
| | | Purified water | | | Balance | | |
| Mass ratio [CGC/surfactant] | | | 0.20 | 0.20 | 0.20 | 0.20 | 0.20 |
| Mass ratio [CGC/oil] | | | 0.08 | 0.07 | 0.06 | 0.03 | 0.02 |
| Mass ratio [surfactant/oil] | | | 0.38 | 0.34 | 0.31 | 0.17 | 0.11 |

TABLE 12-continued

|  |  | Example | | | | |
|---|---|---|---|---|---|---|
|  | Hair cosmetic (conditioner) | 110 | 111 | 106 | 112 | 113 |
| Evaluation | Smoothness at the time of rinsing | 3.4 | 3.8 | 3.6 | 3.8 | 3.4 |
|  | Long-lasting feeling of smoothness | 3.4 | 3.4 | 4.0 | 3.4 | 3.4 |
|  | Moist feeling after drying | 3.4 | 3.8 | 3.6 | 4.6 | 5.0 |
|  | Softness after drying | 3.8 | 3.8 | 4.0 | 4.4 | 3.8 |

*[1] QUARTAMIN 2285E-E (active component: 58%), available from Kao Corporation
*[2] KALCOL 6098, available from Kao Corporation
*[3] KALCOL 8098, available from Kao Corporation
*[4] BY22-029 (active component: 50%), available from Dow Corning Toray Co., Ltd.

TABLE 13

|  |  |  | Example | | | |
|---|---|---|---|---|---|---|
|  |  | Hair cosmetic (conditioner) | 114 | 115 | 116 | 117 |
| Blending composition (parts by mass) | CGC | CGC (6) | 0.3 | 0.3 | 0.3 | 0.3 |
|  | Surfactant | Cetyltrimethylammonium chloride*[1] | 1.5 | | | |
|  |  | Stearoxypropyltrimethylammonium chloride*[2] | | 1.5 | | |
|  |  | Stearamidopropyldimethylamine*[3] | | | 1.5 | |
|  |  | Behenamidopropyldimethylamine*[4] | | | | 1.5 |
|  | Oil | Cetyl alcohol*[5] | 1.3 | 1.3 | 1.3 | 1.3 |
|  |  | Stearyl alcohol*[6] | 2.6 | 2.6 | 2.6 | 2.6 |
|  |  | Highly polymerized dimethyl polysiloxane*[7] | 1.0 | 1.0 | 1.0 | 1.0 |
|  |  | pH regulator | Suitable amount | | | |
|  |  | Purified water | Balance | | | |
| Evaluation |  | Smoothness at the time of rinsing | 4.2 | 3.8 | 3.8 | 3.4 |
|  |  | Long-lasting feeling of smoothness | 3.8 | 4.0 | 3.8 | 3.4 |
|  |  | Moist feeling after drying | 3.6 | 3.6 | 3.6 | 3.4 |
|  |  | Softness after drying | 3.8 | 4.0 | 3.6 | 3.6 |

*[1] QUARTAMIN 60W (active component: 30%), available from Kao Corporation
*[2] QUARTAMIN E-80K (active component: 45%), available from Kao Corporation
*[3] CATINAL MPAS, available from Toho Chemical Industry Co., Ltd.
*[4] CATINAL BMPA, available from Toho Chemical Industry Co., Ltd.
*[5] KALCOL 6098, available from Kao Corporation
*[6] KALCOL 8098, available from Kao Corporation
*[7] BY22-029 (active component: 50%), available from Dow Corning Toray Co., Ltd.

It is noted from Tables 11 to 13 that the conditioners of Examples 104 to 117 are an excellent conditioner capable of imparting smoothness and long-lasting feeling of smoothness at the time of rinsing and moist feeling and softness after drying.

[Evaluation of Skin Cleanser Composition]

Example 118

Body Shampoo

A body shampoo having the following composition was manufactured in the usual way.

After wetting both hands, 0.5 mL of the obtained body shampoo was applied on the both hands and foamed. Thereafter, the both hands were rinsed with running water for 10 seconds, drops of water were wiped off, and a skin touch feeling after drying was evaluated.

As a result, the skin after cleansing with this body shampoo and drying had an excellent moisturizing feeling.

| (Component) | (%) |
|---|---|
| Lauric acid | 8.6 |
| Myristic acid | 8.4 |
| Palmitic acid | 2.5 |
| Sodium polyoxyethylene alkyl ether sulfate*[1] | 2.9 |
| Glycerin | 1.9 |
| Propylene glycol | 1.2 |
| Coconut fatty acid amidopropyl betaine*[2] | 0.9 |
| CGC (6) | 0.3 |
| Potassium hydroxide (amount for adjusting the pH to 9.6) | Suitable amount |
| Perfume and antiseptic | Suitable amount |
| Purified water | Balance |
| Total | 100.0 |

*[1] EMAL 270J, available from Kao Corporation
*[2] AMPHITOL 55AB, available from Kao Corporation

Example 119

Body Shampoo

A body shampoo having the following composition was manufactured in the usual way and then evaluated in the same manner as that in Example 118. As a result, the skin after cleansing with this body shampoo and drying had an excellent moisturizing feeling.

| (Component) | (%) |
|---|---|
| Sodium polyoxyethylene alkyl ether sulfate*¹ | 10.0 |
| Coconut fatty acid amidopropyl betaine*² | 1.5 |
| Coconut fatty acid monoethanolamide | 1.0 |
| Glycerin | 2.0 |
| Sodium chloride | 1.0 |
| CGC (6) | 0.3 |
| Perfume and antiseptic | Suitable amount |
| Purified water | Balance |
| Total | 100.0 |

*¹Trade name: EMAL 270J, available from Kao Corporation
*²Trade name: AMPHITOL 55AB, available from Kao Corporation Example 120

Body Shampoo

A body shampoo having the following composition was manufactured in the usual way and then evaluated in the same manner as that in Example 118. As a result, the skin after cleansing with this body shampoo and drying had an excellent moisturizing feeling.

| (Component) | (%) |
|---|---|
| Potassium lauroyl sarcosinate*¹ | 6.0 |
| Sodium polyoxyethylene alkyl ether sulfate*² | 3.3 |
| Propylene glycol | 3.2 |
| Coconut fatty acid amidopropyl betaine*³ | 2.8 |
| Glycol distearate | 1.0 |
| Coconut fatty acid diethanolamide | 0.7 |
| CGC (6) | 0.3 |
| Perfume and antiseptic | Suitable amount |
| pH regulator (amount for adjusting the pH to 6.0) | Suitable amount |
| Purified water | Balance |
| Total | 100.0 |

*¹NIKKOL SARCOSINATE LK-30, available from Nikko Chemicals Co., Ltd.
*²EMAL 270J, available from Kao Corporation
*³AMPHITOL 55AB, available from Kao Corporation Example 121

Facial Cleanser

A facial cleanser having the following composition was manufactured and then evaluated in the same manner as that in Example 118. As a result, the skin after cleansing with this facial cleanser and drying had an excellent moisturizing feeling.

| (Component) | (%) |
|---|---|
| Sodium methyl cocoyl taurate*¹ | 1.4 |
| Lauric acid | 28.2 |
| Myristic acid | 2.8 |
| Palmitic acid | 3.1 |
| PEG-32*² | 2.0 |
| Glycerin | 16.0 |
| CGC (6) | 0.3 |
| Perfume and antiseptic | Suitable amount |
| pH regulator (amount for adjusting the pH to 9.0) | Suitable amount |
| Purified water: | Balance |
| Total | 100.0 |

*¹NIKKOL CMT-30, available from Nikko Chemicals Co., Ltd.
*²PEG#1500, available from NOF Corporation Example 122

Body Shampoo

A body shampoo having the following composition was manufactured and then evaluated in the same manner as that in Example 118. As a result, the skin after cleansing with this body shampoo and drying had an excellent moisturizing feeling.

| (Component) | (%) |
|---|---|
| Sodium polyoxyethylene alkyl ether sulfate*¹ | 6.2 |
| Sodium cocoyl isethionate*² | 5.8 |
| Coconut fatty acid amidopropyl betaine*³ | 3.7 |
| Glycerin | 3.2 |
| Lauric acid | 4.0 |
| Myristic acid | 0.5 |
| Palmitic acid | 1.5 |
| Stearic acid | 1.5 |
| Sunflower oil | 13.2 |
| CGC (3) | 0.2 |
| Potassium hydroxide (amount for adjusting the pH to 7.3) | Suitable amount |
| Perfume and antiseptic | Suitable amount |
| Purified water | Balance |
| Total | 100.0 |

*¹EMAL 270J, available from Kao Corporation
*²DIAPON CI, available from NOF Corporation
*³AMPHITOL 5BAB, available from Kao Corporation Example 123

Facial Cleanser

A facial cleanser having the following composition was manufactured and then evaluated in the same manner as that in Example 118. As a result, the skin after cleansing with this facial cleanser and drying had an excellent moisturizing feeling.

| (Component) | (%) |
|---|---|
| Sodium cocoyl glycine*¹ | 9.4 |
| Sodium cocoamphoacetate*² | 2.5 |
| Coconut fatty acid amidopropyl betaine*³ | 1.7 |
| Lauric acid | 2.0 |
| Glycerin | 6.0 |
| Vaseline | 9.0 |

-continued

| (Component) | (%) |
|---|---|
| CGC (3) | 0.3 |
| Perfume and antiseptic | Suitable amount |
| pH regulator (amount for adjusting the pH to 7.0) | Suitable amount |
| Purified water | Balance |
| Total | 100.0 |

*[1]Amilite GCS-11, available from Ajinomoto Co., Inc.
*[2]NIKKOL AM-101, available from Nikko Chemicals Co., Ltd.
*[3]AMPHITOL 55AB, available from Kao Corporation

INDUSTRIAL APPLICABILITY

When the cationized glycerolated cellulose according to the present invention is blended in a hair cosmetic such as a hair shampoo, etc., it is able to impart excellent smoothness and its long-lasting feeling at the time of rinsing and to impart a moist feeling and softness to the hair after drying. In addition, when the cationized glycerolated cellulose according to the present invention is blended in a skin cleanser such as a body shampoo, a facial cleanser, etc., it is able to impart an excellent moisturizing feeling after cleansing the skin. Accordingly, a surfactant composition containing the cationized glycerolated cellulose according to the present invention can be suitably used for hair cosmetics or skin cleansers.

The invention claimed is:

1. A surfactant composition comprising: a cationized glycerolated cellulose having a main chain derived from an anhydroglucose represented by the following general formula (1), wherein a degree of substitution of a cationized alkylene oxy group per the anhydroglucose unit is from 0.01 to 0.18, and a degree of substitution of a glycerol group per the anhydroglucose unit is from 0.5 to 5.0, and a viscosity of a 1% by mass aqueous solution at 25° C. is from 10 to 10,000 mPa·s; a surfactant; water; and an oil, wherein the content of the oil is from 0.01 to 30% by mass, and the oil contains a silicone oil,

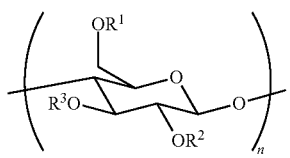

(1)

wherein
each of $R^1$, $R^2$, and $R^3$ independently indicates a substituent composed of one or more repeating units selected among the following formulae (2) to (5), or a hydrogen atom, provided that all of $R^1$, $R^2$, and $R^3$ in the molecule are not a hydrogen atom at the same time; and n indicates an average polymerization degree of the main chain derived from an anhydroglucose and is a number of from 100 to 12,000,

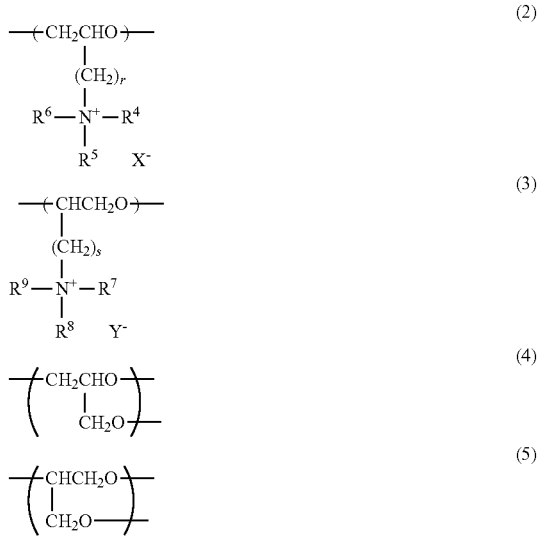

wherein
a repeating unit structure represented by the formula (2) or (3) indicates a cationized alkylene oxy group; a repeating unit structure represented by the formula (4) or (5) indicates a glycerol group; each of $R^4$ to $R^9$ independently indicates a linear or branched alkyl group having a carbon number of from 1 to 3; $X^-$ and $Y^-$ indicate an anion; r and s indicate any integer of from 0 to 3; and in the repeating unit structures represented by the formulae (2) to (5), the oxygen atom is bound to a hydrogen atom or a carbon atom of other repeating unit.

2. The surfactant composition according to claim 1, wherein a degree of substitution of a hydrocarbon group having a carbon number of 7 or more in the cationized glycerolated cellulose is less than 0.01.

3. The surfactant composition according to claim 1, wherein a viscosity of a 1% by mass aqueous solution of the cationized glycerolated cellulose at 25° C. is from 20 to 6,000 m·Pas.

4. The surfactant composition according to claim 1, wherein a degree of substitution of the glycerol group in the cationized glycerolated cellulose is from 1.0 to 2.0.

5. The surfactant composition according to claim 1, wherein the content of the cationized glycerolated cellulose is from 0.01 to 10% by mass.

6. The surfactant composition according to claim 1, wherein a mass ratio of the cationized glycerolated cellulose to the surfactant [(cationized glycerolated cellulose)/(surfactant)] is from 0.0002 to 10.

7. The surfactant composition according to claim 1, wherein the content of the surfactant is from 0.1 to 80% by mass.

8. The surfactant composition according to claim 1, wherein the surfactant is at least one selected from anionic surfactants selected among alkyl sulfates, polyoxyethylene alkyl ether sulfates, polyoxyethylene alkyl ether acetates, alkyl sulfosuccinates, acyl glutamates, acyl isethionates, and acyl methyl taurates; nonionic surfactants selected among polyoxyalkylene alkyl ethers, polyoxyethylene hydrogenated castor oils, fatty acid alkanolamides, and alkyl glucosides; and ampholytic surfactants selected among alkyldimethylamino acetic acid betaines, fatty acid amidopropyl betaines, and alkylhydroxy sulfobetaines.

9. The surfactant composition according to claim 1, wherein a cation charge density of the cationized glycerolated cellulose is 0.05 mmol/g or more and not more than 0.8 mmol/g.

10. The surfactant composition according to claim 1, wherein the content of the oil is from 0.1 to 15% by mass.

11. The surfactant composition according to claim 1, wherein the silicone oil is one or more members selected among dimethylpolysiloxane, dimethylpolysiloxane having a hydroxyl group on an end thereof, dimethylpolysiloxane having an amino group in a molecule thereof, polyether-modified silicone, glyceryl-modified silicone, an amino derivative silicone, a silicone wax, and a silicone elastomer.

12. A method of treating hair by use of the surfactant composition according to claim 1.

13. A method of cleansing skin by use of the surfactant composition according to claim 1.

14. The surfactant composition according to claim 1, wherein the content of the cationized glycerolated cellulose is from 0.1 to 1% by mass.

15. The surfactant composition according to claim 1, wherein a mass ratio of the cationized glycerolated cellulose to the surfactant [(cationized glycerolated cellulose)/(surfactant)] is from 0.005 to 3.

16. The surfactant composition according to claim 1, wherein the content of the surfactant is from 1 to 36% by mass.

17. The surfactant composition according to claim 1, wherein the surfactant is at least one selected from anionic surfactants selected among alkyl sulfates, polyoxyethylene alkyl ether sulfates, polyoxyethylene alkyl ether acetates, alkyl sulfosuccinates, acyl glutamates, acyl isethionates, and acyl methyl taurates.

18. The surfactant composition according to claim 11, wherein the silicone oil is dimethylpolysiloxane.

19. The surfactant composition according to claim 1, wherein a viscosity of the silicone oil is 100,000 $mm^2/s$ or more and not more than 15,000,000 $mm^2/s$.

20. The surfactant composition according to claim 1, wherein a cation charge density of the cationized glycerolated cellulose is 0.3 mmol/g or more and not more than 0.5 mmol/g.

* * * * *